United States Patent
Karavany et al.

(10) Patent No.: US 11,357,610 B2
(45) Date of Patent: *Jun. 14, 2022

(54) AORTIC IMPLANT

(71) Applicant: HEMODYNAMX-TECHNOLOGIES LTD., Modi'in (IL)

(72) Inventors: Sagy Karavany, Kibbutz Dvir (IL); Tanhum Feld, Moshav Merhavya (IL); Boaz Nishri, D.N. Menashe (IL)

(73) Assignee: HEMODYNAMX-TECHNOLOGIES LTD., Modiin (IL)

(*) Notice: Subject to any disclaimer, the term of this patent is extended or adjusted under 35 U.S.C. 154(b) by 90 days.

This patent is subject to a terminal disclaimer.

(21) Appl. No.: 16/743,721

(22) Filed: Jan. 15, 2020

(65) Prior Publication Data
US 2020/0205962 A1 Jul. 2, 2020

Related U.S. Application Data

(63) Continuation of application No. 15/550,661, filed as application No. PCT/IL2016/050170 on Feb. 11, 2016, now Pat. No. 10,568,731.
(Continued)

(51) Int. Cl.
A61F 2/06 (2013.01)
A61F 2/07 (2013.01)
(Continued)

(52) U.S. Cl.
CPC ............ A61F 2/06 (2013.01); A61F 2/07 (2013.01); A61F 2/2418 (2013.01); A61F 2/852 (2013.01);
(Continued)

(58) Field of Classification Search
CPC combination set(s) only.
See application file for complete search history.

(56) References Cited

U.S. PATENT DOCUMENTS 5,139,515 A 8/1992 Robicsek
6,120,534 A 9/2000 Ruiz
(Continued)

FOREIGN PATENT DOCUMENTS

CN 101287424 A 10/2008
EP 1849440 A1 10/2007
(Continued)

OTHER PUBLICATIONS

Extended European Search Report for European Application No. 18878693.3 dated Jul. 8, 2021.
(Continued)

Primary Examiner — Paul B Prebilic
(74) Attorney, Agent, or Firm — Dorsey & Whitney LLP

(57) ABSTRACT

Apparatus and methods are described for regulating blood flow in an ascending aorta of a subject including inserting a device into the ascending aorta. When in a deployed state, the device defines an inner surface that defines a conduit through the device, at least a portion of the inner surface diverging, such that a cross-sectional area of the conduit at the downstream end of the diverging portion is greater than a cross-sectional area of the conduit at the upstream end of the diverging portion. The device is deployed within a longitudinal portion of the ascending aorta, such that the device defines the conduit throughout deployment of the device within the longitudinal portion of the ascending aorta. Other applications are also described.

20 Claims, 10 Drawing Sheets

Related U.S. Application Data

(60) Provisional application No. 62/265,571, filed on Dec. 10, 2015, provisional application No. 62/115,207, filed on Feb. 12, 2015.

(51) Int. Cl.
  *A61F 2/24* (2006.01)
  *A61F 2/852* (2013.01)
  *A61F 2/848* (2013.01)
  *A61F 2/82* (2013.01)

(52) U.S. Cl.
  CPC ......... *A61F 2/848* (2013.01); *A61F 2002/068* (2013.01); *A61F 2002/826* (2013.01); *A61F 2230/0067* (2013.01); *A61F 2250/0003* (2013.01); *A61F 2250/0039* (2013.01)

(56) References Cited

U.S. PATENT DOCUMENTS

| | | | |
|---|---|---|---|
| 7,018,404 | B2 | 3/2006 | Holmberg et al. |
| 7,766,814 | B2 | 8/2010 | Walsh |
| 8,585,572 | B2 * | 11/2013 | Mehmanesh ....... A61M 60/135 600/18 |
| 8,623,065 | B2 | 1/2014 | Lau et al. |
| 8,715,337 | B2 | 5/2014 | Chuter |
| 9,232,992 | B2 | 1/2016 | Heidner et al. |
| 10,368,985 | B2 | 8/2019 | Wilson et al. |
| 10,568,731 | B2 | 2/2020 | Karavany et al. |
| 11,207,200 | B2 * | 12/2021 | Karavany ................. A61F 2/06 |
| 11,224,503 | B2 * | 1/2022 | Karavany ............... A61F 2/966 |
| 2003/0045828 | A1 | 3/2003 | Wilk |
| 2004/0093058 | A1 | 5/2004 | Cottone et al. |
| 2004/0249439 | A1 | 12/2004 | Richter et al. |
| 2004/0260389 | A1 | 12/2004 | Case et al. |
| 2005/0222674 | A1 | 10/2005 | Paine |
| 2006/0009835 | A1 | 1/2006 | Osborne et al. |
| 2006/0106449 | A1 | 5/2006 | Ben |
| 2006/0149360 | A1 | 7/2006 | Schwammenthal et al. |
| 2006/0259134 | A1 | 11/2006 | Schwammenthal et al. |
| 2007/0185565 | A1 | 8/2007 | Schwammenthal et al. |
| 2007/0293808 | A1 | 12/2007 | Williams et al. |
| 2008/0071361 | A1 | 3/2008 | Tuval et al. |
| 2008/0071363 | A1 | 3/2008 | Tuval et al. |
| 2009/0105805 | A1 | 4/2009 | Baker et al. |
| 2009/0210047 | A1 | 8/2009 | Amplatz et al. |
| 2009/0222078 | A1 | 9/2009 | Greenberg |
| 2009/0240320 | A1 | 9/2009 | Tuval et al. |
| 2009/0270965 | A1 | 10/2009 | Sinha et al. |
| 2010/0023046 | A1 * | 1/2010 | Heidner ........... A61B 17/12172 606/191 |
| 2010/0145433 | A1 | 6/2010 | Anukhin et al. |
| 2011/0288634 | A1 | 11/2011 | Tuval et al. |
| 2012/0010690 | A1 | 1/2012 | Richter et al. |
| 2012/0022629 | A1 | 1/2012 | Perera et al. |
| 2013/0013053 | A1 | 1/2013 | Hartley et al. |
| 2013/0144383 | A1 | 6/2013 | Thill et al. |
| 2013/0178750 | A1 | 7/2013 | Sheehan et al. |
| 2014/0257474 | A1 | 9/2014 | Roeder |
| 2015/0238315 | A1 | 8/2015 | Rabito et al. |
| 2015/0366693 | A1 | 12/2015 | Kagan et al. |
| 2017/0042551 | A1 | 2/2017 | Celermajer et al. |
| 2018/0036109 | A1 | 2/2018 | Karavany et al. |
| 2018/0353281 | A1 * | 12/2018 | Nussinovitch ............ A61F 2/04 |
| 2019/0183629 | A1 | 6/2019 | Karavany et al. |
| 2021/0169634 | A1 | 6/2021 | Karavany et al. |

FOREIGN PATENT DOCUMENTS

| | | |
|---|---|---|
| EP | 2777618 A1 | 9/2014 |
| EP | 2896387 A1 | 7/2015 |
| EP | 2785277 B1 | 4/2017 |
| JP | 2001527453 A | 12/2001 |
| JP | 2007526789 A | 9/2007 |
| JP | 2008537891 A | 10/2008 |
| JP | 2011502628 A | 1/2011 |
| WO | 9852476 A1 | 11/1998 |
| WO | 03028522 A2 | 4/2003 |
| WO | 2005002466 A2 | 1/2005 |
| WO | 2005084730 A1 | 9/2005 |
| WO | 2006070372 A2 | 7/2006 |
| WO | 2006080010 A2 | 8/2006 |
| WO | 2009061419 A1 | 5/2009 |
| WO | 2012018590 A1 | 2/2012 |
| WO | 2015013344 A2 | 1/2015 |
| WO | 2016128983 A1 | 8/2016 |
| WO | 2018029688 A1 | 2/2018 |
| WO | 2018220589 A1 | 12/2018 |
| WO | 2019097424 A2 | 5/2019 |
| WO | 2020234787 A1 | 11/2020 |

OTHER PUBLICATIONS

Notice of Allowance for U.S. Appl. No. 16/322,047 dated Sep. 14, 2021.
Notice of Allowance for U.S. Appl. No. 16/763,884 dated Aug. 16, 2021.
Examination Report for Indian Application No. 201717029373 dated Oct. 8, 2020.
International Search Report and Written Opinion from International Application No. PCT/IB2020/054761 dated Aug. 18, 2020.
Issue Notification for U.S. Appl. No. 15/550,661 dated Feb. 5, 2020.
Office Action for Chinese Application No. 201780049360.2 dated Oct. 10, 2020.
Supplemental Notice of Allowability for U.S. Appl. No. 15/550,661 dated Jan. 23, 2020.
U.S. Appl. No. 16/322,047, filed Jan. 30, 2019.
U.S. Appl. No. 16/763,884, filed May 13, 2020.
U.S. Appl. No. 62/586,258, filed Nov. 15, 2017.
U.S. Appl. No. 62/630,406, filed Feb. 14, 2018.
Chinese Office Action for Chinese Application No. 201680015323.5 dated Dec. 14, 2018.
European Search Report for European Application No. 16748842.8 dated Sep. 19, 2018.
Final Office Action for U.S. Appl. No. 15/550,661 dated Jun. 19, 2019.
International Search Report and Written Opinion from International Application No. PCT/IB2018/058961 dated May 8, 2019.
International Search Report and Written Opinion from International Application No. PCT/IL2016/050170 dated Jun. 10, 2016.
International Search Report and Written Opinion from International Application No. PCT/IL2017/050884 dated Oct. 30, 2017.
Japanese Office Action for Japanese Application No. 2017-542883 dated Dec. 10, 2019.
Non-Final Office Action for U.S. Appl. No. 15/550,661 dated Aug. 6, 2019.
Non-Final Office Action for U.S. Appl. No. 15/550,661 dated Feb. 20, 2019.
Notice of Allowance for U.S. Appl. No. 15/550,661 dated Oct. 17, 2019.
Protege webpage—downloaded Mar. 19, 2015.
Restriction Requirement for U.S. Appl. No. 15/550,661 dated Dec. 4, 2018.
U.S. Appl. No. 15/550,661, filed Aug. 11, 2017.
U.S. Appl. No. 62/115,207, filed Feb. 12, 2015.
U.S. Appl. No. 62/265,571, filed Dec. 10, 2015.
U.S. Appl. No. 62/373,993, filed Aug. 12, 2016.
Heinrich, et al., "Experimental analysis of fluid mechanical energy losses in aortic valve stenosis: importance of pressure recovery", Annals of biomedical engineering, 24.6, 1996, pp. 685-694.
Non-Final Office Action for U.S. Appl. No. 16/322,047 dated Mar. 3, 2021.
Office Action for Chinese Application No. 201780049360.2 dated May 25, 2021.
Office Action for Chinese Application No. 201910988467.4 dated May 24, 2021.

(56) References Cited

OTHER PUBLICATIONS

Issue Notification for U.S. Appl. No. 16/322,047 dated Dec. 28, 2021.
Issue Notification for U.S. Appl. No. 16/763,884 dated Dec. 8, 2021.
U.S. Appl. No. 17/526,053, filed Nov. 15, 2021.
U.S. Appl. No. 62/850,656, filed May 21, 2019.

* cited by examiner

AORTIC IMPLANT

CROSS-REFERENCE TO RELATED APPLICATIONS

The present application is a continuation of U.S. application Ser. No. 15/550,661 to Karavany (published as 2018/0036109) filed on 11 Aug. 2017, now U.S. Pat. No. 10,568,731 which is a U.S. National Phase of PCT International Application No. PCT/IL2016/050170 to Karavany (published as WO 16/128983), filed 11 Feb. 2016, which claims priority from:

U.S. Provisional Application No. 62/115,207 to Karavany, filed 12 Feb. 2015, entitled "Aortic implant," and U.S. Provisional Application No. 62/265,571 to Karavany, filed 10 Dec. 2015, entitled "Aortic implant."

U.S. Provisional Application No. 62/115,207 and U.S. Provisional Application No. 62/265,571 are incorporated herein by reference.

FIELD OF EMBODIMENTS OF THE INVENTION

Some applications of the present invention generally relate to medical apparatus. Specifically, some applications of the present invention relate to an aortic implant and methods of use thereof.

BACKGROUND

Aortic valve stenosis is a common disease in which calcification of the cusps of the aortic valve cause the flexibility of the valve to be compromised and the open valve area to diminish. Once aortic valve stenosis develops, due to the reduction in the aortic valve diameter, blood flow is compromised. Aortic valve stenosis often progresses to heart failure and other life threatening conditions.

SUMMARY OF EMBODIMENTS

For some applications of the present invention, a device is deployed inside a blood vessel of a subject. The device defines an inner surface that defines a conduit through the device that passes from the proximal end of the device to the distal end of the device. At least a portion of the conduit diverges in a direction from a proximal (i.e., upstream) end of the conduit to a distal (i.e., downstream) end of the conduit, such that the cross-sectional area of the conduit at its distal (i.e., downstream) end is greater than the cross-sectional area of the conduit at its proximal (i.e., upstream) end. The device is deployed within a longitudinal portion of the blood vessel, such that blood flow through the longitudinal portion of the blood vessel, via any flow path other than through the conduit, whether in the antegrade or retrograde direction, is less than 20 percent (e.g., less than 10 percent, or less than 5 percent) of the total blood flow through the longitudinal portion of the blood vessel. The divergence of the conduit is configured to reduce pressure loss of blood flowing through the conduit, relative to the loss of pressure of the blood flowing through the longitudinal portion of the blood vessel in the absence of the device. The divergence of the conduit is configured to reduce the blood pressure loss by reducing the area of flow separation.

The device is typically placed in the ascending aorta of a subject suffering from aortic valve stenosis, in the vicinity of the stenosed aortic valve. The blood exiting the subject's left ventricle is directed into the conduit and the conduit is shaped such as to reduce blood pressure loss by reducing the area of flow separation, as described hereinabove. Typically, by directing the blood to flow in the above-described manner, loss of pressure and energy of the blood flow exiting the left ventricle into the ascending aorta is reduced relative to loss of pressure and energy of the blood flow in the absence of the device. Thus, placement of the device in the subject's ascending aorta may decrease the subject's left ventricular pressure, reduce afterload, and/or and improve the subject's cardiac output. For some applications, regulating the blood flow from the aortic valve in the above-described manner may postpone or stop the degradation process leading to further aortic valve stenosis. An unhealthy flow regime in the ascending aorta can cause sequential deposits of thrombi on the valve surface that can cause further valve thickening, deformation and calcification leading to severe stenosis. The deployed device, by changing the flow regime, may reduce the inflammatory process that causes calcification. Thus, the device may decrease the degradation of the medical situation of the subject.

The device typically defines one or more surfaces that extend from the outside of the conduit to the inner wall of the blood vessel, and/or to an outer support structure that is in contact with the inner wall of the blood vessel. Typically, the one or more surfaces extend radially outward, around the full circumference of the conduit, from the conduit at least to the radial location of the inner surface of the outer support structure (such that the surface extends to the inner surface of the blood vessel, and/or to the outer support structure). The surfaces are configured to impede backflow of blood around the outside of the conduit (e.g., the distal end of the conduit), in the manner described herein.

Typically, the device defines a proximal outer surface that surrounds a proximal portion of the conduit. For some applications, the device defines a distal outer surface that surrounds a distal portion of the conduit. Typically, the surfaces extend from the outside of the conduit to the inner wall of the blood vessel, and/or to an outer support structure that is in contact with the inner wall of the blood vessel. The proximal and distal outer surfaces are configured such that, when the device is deployed inside a longitudinal portion of the subject's aorta, the surfaces substantially impede blood flow through the longitudinal portion of the aorta, whether in the antegrade or the retrograde direction, via any flow path other than through the conduit defined by the inner surface of the device. For example, the proximal and distal surfaces may be configured such that, when the device is deployed inside the longitudinal portion of the subject's aorta, flow via flow paths other than through the conduit defined by the inner surface of the device is less than 20 percent (e.g., less than 10 percent, or less than 5 percent) of total blood flow through the longitudinal portion of the subject's aorta.

For some applications, the device does not define a separate distal outer surface. Rather, the distal end of the inner surface that defines the conduit extends to the inner surface of the blood vessel, or to the outer support structure, such that the distal end of the inner surface impedes the backflow of blood around the outside of the distal end of the conduit. In this manner, the distal end of the inner surface acts as the distal outer surface.

For some applications, the proximal and distal outer surfaces and/or the inner surface are impermeable and prevent blood from flowing back toward the aortic valve during systole (and/or during diastole), around the outside of the conduit. By preventing blood from flowing back toward the aortic valve during systole, the surfaces prevent loss of pressure and energy of the blood flow exiting the left ventricle into the ascending aorta relative to loss of pressure and energy of the blood flow in the absence of the device. For some applications, the surfaces are not impermeable, but have a permeability that is sufficiently low as to substantially impede blood from flowing through the longitudinal portion of the aorta, via any flow path other than through the conduit defined by the inner surface of the device, in the manner described hereinabove.

For some applications, the device is configured to promote coagulation of blood that is disposed within a region between the conduit and the inner wall of the aorta within the longitudinal portion of the aorta in which the device is placed, by substantially reducing blood flow through this region relative to in the absence of the device. Typically, the material that defines the proximal, distal, and/or inner surfaces is configured to prevent any thrombi that develop within the region from exiting the region and entering the subject's bloodstream. For some applications, by promoting the coagulation of blood within the region, the device causes blood entering the region to become coagulated, such that the region becomes filled with coagulated blood within a given time period of the device being placed within the aorta (e.g., within one week, one month, or three months of the device being placed within the aorta), such that the coagulated blood impedes (e.g., blocks) the flow of blood through the region. For some application, the blood that becomes coagulated within the region is blood that became trapped within the region immediately upon deployment of the device. Alternatively or additionally, blood enters the region subsequent to the device having been deployed, and the blood that subsequently enters the region becomes coagulated.

It is noted that, typically, the device does not include a prosthetic valve disposed within the conduit or at any other location within the device. The device typically performs all of the functions described herein without requiring the use of a prosthetic valve of any type.

The terms "proximal" and "distal" as used in the present application refer to the location of the respective elements in the aorta with respect to the aortic valve. That is, the term "proximal" refers to an element that is "upstream" and closer to the aortic valve, and the term "distal" refers to an element that is "downstream" and further from the aortic valve. Thus, the term "proximal" is used synonymously with the term "upstream" and the term "distal" is used synonymously with the term "downstream." In cases in which the device is placed in a different position within the subject's body, the terms "proximal" and "distal" are to be understood with respect to the direction of blood flow, a location that is relatively upstream being considered "proximal" and a location that is relatively downstream being considered "distal."

There is therefore provided, in accordance with some applications of the present invention, a method for regulating blood flow in an ascending aorta of a subject, the method including:

inserting, into the ascending aorta, a device that, when in a deployed state, defines an inner surface that defines a conduit through the device from an upstream end of the device to a downstream end of the device, at least a portion of the inner surface diverging in a direction from an upstream end of the diverging portion to a downstream end of the diverging portion, such that a cross-sectional area of the conduit at the downstream end of the diverging portion is greater than a cross-sectional area of the conduit at the upstream end of the diverging portion; and deploying the device within a longitudinal portion of the ascending aorta, such that blood flow through the longitudinal portion of the ascending aorta, via any flow path other than through the conduit, is less than 20 percent of total blood flow through the longitudinal portion of the ascending aorta.

For some applications, the device does not include a prosthetic valve, and inserting the device into the ascending aorta does not include inserting a prosthetic valve into the ascending aorta.

For some applications, deploying the device within the longitudinal portion of the ascending aorta includes deploying the device within the longitudinal portion of the ascending aorta such that there is no blood flow through the longitudinal portion of the aorta, via any flow path other than through the conduit.

For some applications, inserting the device into the ascending aorta includes inserting the device into the ascending aorta, a portion of the inner surface that is proximal to the diverging portion of the conduit, defining a converging portion of the conduit that converges in a direction from an upstream end of the converging portion to a downstream end of the converging portion.

For some applications, the device includes a set of one or more balloons, and deploying the device includes inflating the one or more balloons.

For some applications, the method further includes identifying the subject as suffering from an aortic valve stenosis, and deploying the device includes treating the subject by reducing pressure loss within the ascending aorta relative to pressure loss within the ascending aorta in an absence of the device.

For some applications, inserting the device into the ascending aorta includes inserting the device into the ascending aorta, the device having a length of more than 20 mm, when in the deployed state. For some applications, inserting the device into the ascending aorta includes inserting the device into the ascending aorta, the length of the device being less than 70 mm.

For some applications, inserting the device into the ascending aorta includes inserting the device into the ascending aorta, a ratio of a diameter of the conduit at the downstream end of the diverging portion to a diameter of the conduit at the upstream end of the diverging portion being greater than 4:3, when the device is in the deployed state. For some applications, inserting the device into the ascending aorta includes inserting the device into the ascending aorta, the ratio of the diameter of the conduit at the downstream end of the diverging portion to the diameter of the conduit at the upstream end of the diverging portion being greater than 2:1. For some applications, inserting the device into the ascending aorta includes inserting the device into the ascending aorta, the ratio of the diameter of the conduit at the downstream end of the diverging portion to the diameter of the conduit at the upstream end of the diverging portion being less than 4:1.

For some applications, inserting the device into the ascending aorta includes inserting the device into the ascending aorta, a difference between a diameter of the conduit at the downstream end of the diverging portion to a diameter of the conduit at the upstream end of the diverging portion being greater than 3 mm, when the device is in the deployed state. For some applications, inserting the device into the ascending aorta includes inserting the device into the ascending aorta, the difference between the diameter of the conduit at the downstream end of the diverging portion to the diameter of the conduit at the upstream end of the diverging portion being greater than 5 mm. For some applications, inserting the device into the ascending aorta includes inserting the device into the ascending aorta, the difference between the diameter of the conduit at the downstream end of the diverging portion to the diameter of the conduit at the upstream end of the diverging portion being less than 30 mm.

For some applications, inserting the device into the ascending aorta includes inserting the device into the ascending aorta, the device including an outer support structure configured to anchor the device inside the ascending aorta by contacting an inner wall of the ascending aorta. For some applications, inserting the device into the ascending aorta includes inserting the device into the ascending aorta, the inner surface and the outer support structure being made of stent graft material. For some applications, inserting the device into the ascending aorta includes inserting the device into the ascending aorta, the inner surface and the outer support structure being made of respective, separate pieces of stent graft material. For some applications, inserting the device into the ascending aorta includes inserting the device into the ascending aorta, the inner surface and the outer support structure being made of a single continuous piece of stent graft material.

For some applications, deploying the device within the longitudinal portion of the ascending aorta, such that blood flow through the longitudinal portion of the ascending aorta, via any flow path other than through the conduit, is less than 20 percent of total blood flow through the longitudinal portion of the ascending aorta includes deploying the device such that a surface of the device extends radially outward around a full circumference of the conduit, and contacts a location selected from the group consisting of: an inner wall of the aorta and an outer support structure of the device that is in contact with the inner wall of the aorta, the surface being configured to impede blood flow therethrough.

For some applications, deploying the device such that the surface of the device contacts the selected location includes deploying the device such that a surface of the device that has a permeability per unit length of less than 0.25 micrometers contacts the selected location.

For some applications, deploying the device such that the surface of the device extends radially outward around the full circumference of the conduit and contacts the selected location includes deploying the device such that a downstream end of the inner surface that defines the conduit extends radially outward around the full circumference of the conduit and contacts the selected location.

For some applications, deploying the device such that the surface of the device extends radially outward around the full circumference of the conduit and contacts the selected location includes deploying the device such that a surface that is disposed around the full circumference of the conduit at the downstream end of the conduit and that extends radially outward contacts the selected location.

For some applications, deploying the device such that the surface of the device extends radially outward around the full circumference of the conduit and contacts the selected location includes deploying the device such that a surface extends radially outward around the full circumference of the conduit and contacts the selected location, the surface being disposed around the conduit at a longitudinal location such that at least a portion of the surface is within a proximal-most 30 percent of a length of the conduit.

For some applications, deploying the device within the longitudinal portion of the ascending aorta, such that blood flow through the longitudinal portion of the ascending aorta, via any flow path other than through the conduit, is less than 20 percent of total blood flow through the longitudinal portion of the ascending aorta includes deploying the device such that two surfaces of the device extend radially outward around the full circumference of the conduit and contact the selected location, both of the surfaces being configured to impede blood flow therethrough. For some applications, deploying the device such that two surfaces of the device extend radially outward around the full circumference of the conduit and contact the selected location includes causing blood to coagulate in a region between the two surfaces. For some applications, the method further includes injecting filling material into a region between the two surfaces.

There is additionally provided, in accordance with some applications of the present invention, apparatus including:

an implantable device configured to be deployed in a blood vessel of a subject, the device including:
    an inner surface that, when the device is in a deployed state within the longitudinal portion of the blood vessel, is configured to define a conduit through the device from a proximal end of the device to a distal end of the device, at least a portion of the conduit diverging in a direction from a proximal end of the conduit to a distal end of the conduit, such that a cross-sectional area of the conduit at its distal end is greater than the cross-sectional area of the conduit at its proximal end; and
    an outer support structure configured to maintain the device within the blood vessel by contacting an inner wall of the blood vessel, the device, when in the deployed state within the longitudinal portion of the blood vessel, being configured to define, at its distal end, a surface extending radially outward, around a full circumference of the conduit, from the conduit at least to a radial location of an inner surface of the outer support structure.

For some applications, the device does not include a prosthetic valve.

For some applications, the surface that extends radially outward has a permeability per unit length of less than 0.25 micrometers.

For some applications, the surface that extends radially outward includes a distal end of the inner surface that defines the conduit.

For some applications, the surface that extends radially outward includes a surface that is disposed around a distal end of the conduit and that extends radially outward.

For some applications, the apparatus further includes an additional surface that:
    when the device is in the deployed state within the longitudinal portion of the blood vessel, is configured to extend radially outward, around the full circumference of the conduit, at least to the radial location of the inner surface of the outer support structure, and
    is disposed around the conduit at a longitudinal location such that at least a portion of the surface is within a proximal-most 30 percent of a length of the conduit.

For some applications, the device is configured such that, when the device is in the deployed state within the longitudinal portion of the blood vessel, a ratio between an outer diameter of a proximal end of the outer support structure and an outer diameter of a distal end of the outer support structure is between 3:4 and 4:3.

For some applications, the device is configured such that, upon the device being implanted within a longitudinal portion of an ascending aorta of the subject, the device reduces pressure loss within the ascending aorta relative to pressure loss within the ascending aorta in an absence of the device.

For some applications, the inner surface is configured to define a proximal converging portion that is proximal to the diverging portion of the conduit, the proximal converging portion converging in a direction from a proximal end of the converging portion to a distal end of the converging portion.

For some applications, the device includes a set of one or more balloons.

For some applications, the device is configured such that, when the device is in the deployed state within the longitudinal portion of the blood vessel, the device has a length of more than 20 mm. For some applications, the device is configured such that the length of the device is less than 70 mm.

For some applications, the device is configured such that, when the device is in the deployed state within the longitudinal portion of the blood vessel, a difference between a diameter of the conduit at the proximal end of the diverging portion to a diameter of the conduit at the distal end of the diverging portion is greater than 3 mm. For some applications, the device is configured such that the difference between the diameter of the conduit at the distal end of the diverging portion to the diameter of the conduit at the proximal end of the diverging portion is greater than 5 mm. For some applications, the device is configured such that the difference between the diameter of the conduit at the distal end of the diverging portion to the diameter of the conduit at the distal end of the diverging portion is less than 30 mm.

For some applications, the device is configured such that, upon the device being implanted within a longitudinal portion of the blood vessel, blood flow through the longitudinal portion of the blood vessel, via any flow path other than through the conduit, is less than 20 percent of total blood flow through the longitudinal portion of the blood vessel. For some applications, the device is configured such that, upon the device being implanted within a longitudinal portion of the blood vessel, there is no blood flow through the longitudinal portion of the blood vessel, via any flow path other than through the conduit.

For some applications, the inner surface and the outer support structure are made of stent graft material. For some applications, the inner surface and the outer support structure are made of respective, separate pieces of stent graft material. For some applications, the inner surface and the outer support structure are made of a single continuous piece of stent graft material.

For some applications, the device is configured such that, when the device is in the deployed state within the longitudinal portion of the blood vessel, the device defines two surfaces that extend radially outward, around the full circumference of the conduit, at least to the radial location of the inner surface of the outer support structure and that are configured to impede blood flow. For some applications, the two surfaces are configured to cause blood to coagulate in a region between the two surfaces. For some applications, the apparatus further includes a filling material configured to be injected into a region between the two surfaces.

For some applications, the device is configured such that, when the device is in the deployed state within the longitudinal portion of the blood vessel, a ratio of a diameter of the conduit at a distal end of the diverging portion to a diameter of the conduit at a proximal end of the diverging portion is greater than 4:3. For some applications, the device is configured such that the ratio of the diameter of the conduit at the distal end of the diverging portion to the diameter of the conduit at the proximal end of the diverging portion is greater than 2:1. For some applications, the device is configured such that the ratio of the diameter of the conduit at the distal end of the diverging portion to the diameter of the conduit at the proximal end of the diverging portion is less than 4:1.

There is further provided, in accordance with some applications of the present invention, apparatus including:

a set of one or more balloons configured to be inflated in a blood vessel of a subject, the set of balloons defining:
  an inner surface that, when the set of balloons is in an inflated state within the blood vessel, is configured to define a conduit through the set of balloons from a proximal end of the set of balloons to the distal end of the set of balloons, at least a portion of the conduit diverging in a direction from a proximal end of the conduit to a distal end of the conduit, such that a cross-sectional area of the conduit at its distal end is greater than the cross-sectional area of the conduit at its proximal end; and
  proximal and distal outer surfaces configured to impede blood flow around the outside of the conduit.

The present invention will be more fully understood from the following detailed description of embodiments thereof, taken together with the drawings, in which:

DETAILED DESCRIPTION OF EMBODIMENTS

Figure 1A:
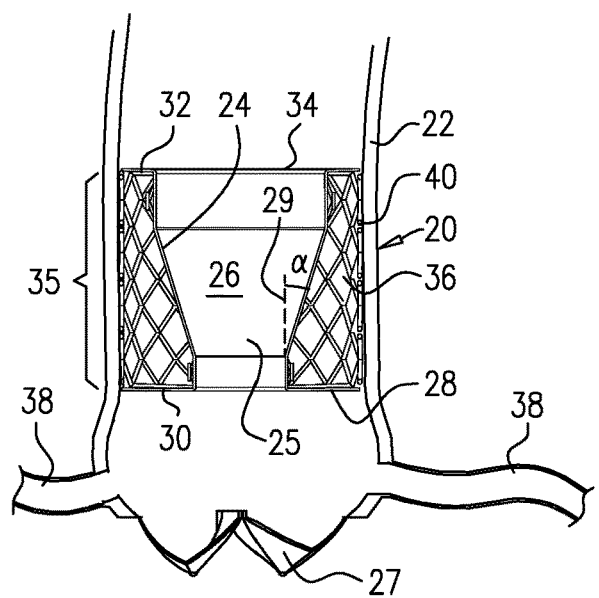
FIGS. 1A-D are schematic illustrations of an implantable device deployed inside a subject's ascending aorta, in accordance with some applications of the present invention.
Figure 1B:
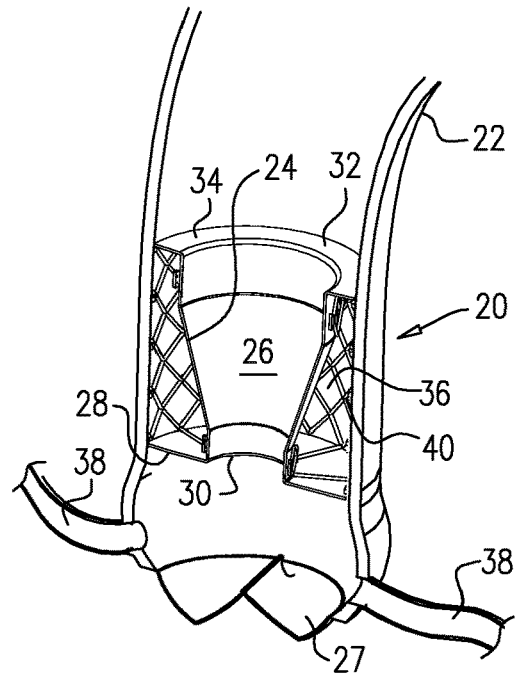
Figure 1C:
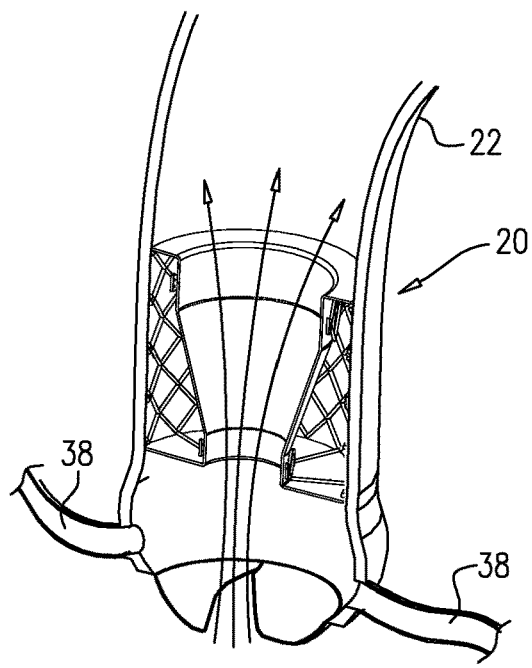
Figure 1D:
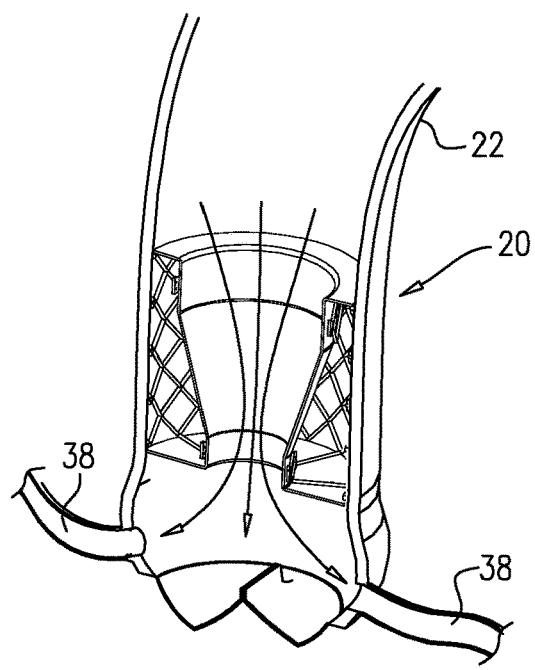

Reference is now made to FIGS. 1A-D, which are schematic illustrations of an implantable device 20 deployed inside a blood vessel of a subject (typically the subject's ascending aorta 22, as shown), in accordance with some applications of the present invention. FIGS. 1C and 1D shows arrows representing blood flow during systole and diastole, respectively. As shown, device 20 defines an inner surface 24 that defines a conduit 26 through the device, from the proximal end of the device to the distal end of the device. At least a portion 25 of the conduit diverges in a direction from a proximal end of the conduit to a distal end of the conduit, such that the cross-sectional area of the conduit at the downstream end is greater than the cross-sectional area of the conduit at the upstream end. The device is typically placed in the ascending aorta of a subject suffering from aortic valve stenosis, in the vicinity of the stenosed aortic valve 27. The blood exiting the subject's left ventricle, during systole, is directed into the conduit (FIG. 1C). The divergence of the conduit is configured to reduce pressure loss of blood flowing through the conduit, relative to the loss of pressure of the blood flowing through the longitudinal portion of the blood vessel in the absence of the device. The conduit reduces the blood pressure loss by reducing the area of flow separation. During diastole, blood flows back toward coronary arteries 38 via conduit 26 (FIG. 1D).

The device is typically deployed within a longitudinal portion of the aorta, such that blood flow through the longitudinal portion of the aorta, via any flow path other than through the conduit, whether in the antegrade or retrograde direction, is less than 20 percent (e.g., less than 10 percent, or less than 5 percent) of the total blood flow through the longitudinal portion of the blood vessel.

Typically, by directing the blood to flow in the above-described manner, loss of pressure and energy of the blood flow exiting the left ventricle into the ascending aorta is reduced relative to the loss of pressure and energy of the blood flow in the absence of the device. Thus, placement of device 20 in the subject's ascending aorta may decrease the subject's left ventricular pressure, reduce afterload, and/or and improve the subject's cardiac output. For some applications, regulating the blood flow from the aortic valve in the above-described manner may postpone or stop the degradation process leading to further aortic valve stenosis. An unhealthy flow regime in the ascending aorta can cause sequential deposits of thrombi on the valve surface that can cause further valve thickening, deformation and calcification leading to severe stenosis. Device 20, by changing the flow regime, may reduce the inflammatory process that cause the calcification. Thus, device 20 may decrease the degradation of the medical situation of the subject.

It is noted that, typically, device 20 does not include a prosthetic valve disposed within the conduit or at any other location within the device. The device typically performs all of the functions described herein without requiring the use of a prosthetic valve of any type.

The device typically defines one or more surfaces (28, 32) that extend from the outside of the conduit to the inner wall of the blood vessel, and/or to an outer support structure 40 that is in contact with the inner wall of the blood vessel. Typically, the one or more surfaces extend radially outward, around the full circumference of the conduit, from the conduit at least to the radial location of the inner surface of the outer support structure (such that the surface extends to the inner surface of the blood vessel, and/or to the outer support structure). The surfaces are configured to impede the backflow of blood, around the outside of the conduit 26 (e.g., around the distal end of conduit 26), toward the aortic valve.

For some applications, the device prevents any backflow of blood, around the outside of the conduit, toward the aortic valve.

Device 20 typically defines a proximal outer surface 28 that surrounds a proximal portion of conduit 26, and that extends at least from outside the conduit to outer support structure 40. For example, as shown in FIG. 1A-D, the proximal outer surface may be a disc-shaped surface that surrounds the proximal end 30 of conduit 26. Typically, the proximal outer surface is disposed around the conduit at a longitudinal location such that at least a portion of the proximal surface is within the proximal-most 30 percent (e.g., the proximal-most 20 percent) of the length of the conduit.

For some applications, device 20 defines a distal outer surface 32 that surrounds a distal portion of conduit 26, and that extends from outside the conduit to outer support structure 40. For example, as shown in FIG. 1A-D, the distal outer surface may be a disc-shaped surface that surrounds distal end 34 of the conduit. For some applications, the device does not define a separate distal outer surface. Rather, the distal end of the inner surface that defines the conduit extends to the inner wall of the blood vessel or to the outer support structure, which is in contact with the inner wall of the blood vessel. In this manner, the distal end of the inner surface acts as the distal outer surface, and impedes the backflow of blood around the outside of the distal end of the conduit, as shown in FIGS. 6A-E.

The proximal and distal outer surfaces are typically configured such that, when device 20 is deployed inside a longitudinal portion 35 of the subject's aorta, the surfaces substantially impede blood flow through longitudinal portion 35, via any flow path other than through conduit 26. For example, the proximal and distal surfaces may be configured such that, when the device is deployed inside the longitudinal portion of the subject's aorta, flow via flow paths other than through the conduit defined by the inner surface of the device, whether in the antegrade or retrograde direction, is less than 20 percent (e.g., less than 10 percent, or less than 5 percent) of total blood flow through the longitudinal portion of the subject's aorta.

For some applications, (a) distal outer surface 32 is configured to impede the backflow of blood around the outside of conduit 26, and (b) proximal outer surface 28 is configured to impede antegrade blood flow around the outside of conduit 26. For example, proximal outer surface 28 may be configured to impede antegrade blood flow around the outside of the conduit, in order to reduce a likelihood of eddy currents and/or stagnated blood forming in the region surrounding the conduit. For some applications, the device includes a distal outer surface (or, the distal end of the inner surface that defines the conduit extends to the inner wall of the blood vessel or to the outer support structure, such that the distal end of the inner surface acts as the distal outer surface), and the device does not include a proximal outer surface, e.g., as described hereinbelow with reference to FIGS. 10A-B.

For some applications, the proximal outer surface, the distal outer surface, and/or the inner surface is impermeable and prevents blood from flowing back toward the aortic valve during systole (and/or during diastole), outside of the conduit. For some applications, by virtue of having both proximal and distal outer surfaces (or a proximal outer surface and an inner surface that extends to the inner wall of the blood vessel), the device is configured to trap any blood that is disposed within a region 36 between the conduit and the inner wall of the aorta within the longitudinal portion of the aorta in which the device is placed. In this manner, the device is configured to prevent any thrombi that develop within region 36 from exiting the region and entering the subject's bloodstream.

As described hereinabove, for some applications, the surfaces are not impermeable, but have a permeability that is sufficiently low as to substantially prevent any blood from flowing through the longitudinal portion of the aorta, via any flow path other than through the conduit defined by the inner surface of the device, in the manner described hereinabove.

For some applications, each of the surfaces has permeability per unit length of less than 0.25 micrometers (i.e., between 0 and 0.25 micrometers), where the permeability per unit length is defined based upon the following equation, which is based upon Darcy's Law: $k/\Delta x = V\mu/\Delta p$ where k is permeability, $\Delta x$ is length (in meters), V is average velocity (in meters per second), $\mu$ is fluid viscosity (measured in Pascal-seconds), and $\Delta P$ is the pressure differential measured in Pascals).

For some applications, the proximal outer surface, the distal outer surface and/or the inner surface includes a material (such as a fabric, a metal, or an alloy) that is structured such that there are open spaces between portions of the material. For example, the material may be arranged in a lattice structure, a braided structure, a criss-cross structure, a woven structure, a cellular structure, a stitched structure, or a similar structure. Typically, even for such applications, more than 20 percent of the area of each of the surfaces is filled with material, and less than 80 percent of the area of each of the surfaces is open space between the material. Further typically, more than 50 percent, e.g., more than 80 percent, of the area of each of the surfaces is filled with material. For some applications, there are no open spaces within the surfaces (i.e., the entirety of each of the surfaces is filled with material).

For some applications, the device is configured to promote coagulation of blood that is disposed within a region between the conduit and the inner wall of the aorta within the longitudinal portion of the aorta in which the device is placed, by substantially reducing blood flow through this region relative to in the absence of the device. Typically, the material that defines the proximal outer surface, the distal outer surface and/or the inner surface is configured to prevent any thrombi that develop within the region from exiting the region and entering the subject's bloodstream. For some applications, by promoting the coagulation of blood within the region, the device causes blood entering the region to become coagulated, such that the region becomes filled with coagulated blood within a given time period of the device being placed within the aorta (e.g., within one week, one month, or three months of the device being placed within the aorta), such that the coagulated blood impedes (e.g., blocks) the flow of blood through the region.

For some application, the blood that becomes coagulated within the region is blood that became trapped within the region immediately upon deployment of the device. Alternatively or additionally, blood enters the region subsequent to the device having been deployed, and the blood that subsequently enters the region becomes coagulated. It is noted that, even for such applications, the proximal and distal surfaces are configured such that, even when the device is first deployed and before coagulated blood has formed inside the region, flow via flow paths other than through the conduit defined by the inner surface of the device is less than 20 percent (e.g., less than 10 percent, or less than 5 percent) of total blood flow through the longitudinal portion of the subject's aorta. For some applications, techniques are applied in order to coagulate blood that is trapped within region 36. For example, coil compaction techniques may be applied in order to cause the blood to coagulate.

Typically, when device 20 is deployed inside the subject's ascending aorta, blood is supplied to the subject's coronary arteries 38 via backflow of blood through conduit 26 during diastole (FIG. 1D), and/or via blood flowing directly from the aortic valve to the coronary arteries without passing into conduit 26 (not shown). For some applications, a portion of the blood supply to the coronary arteries is provided by antegrade blood flow from the aortic valve to the coronary arteries (e.g., during systole). Typically, most of the blood supply to the coronary arteries is via the backflow of blood through conduit 26 during diastole.

As stated above, at least portion 25 of conduit 26 diverges in a direction from proximal end 30 of the conduit to distal end 34 of the conduit. Due to the divergence of the portion of the conduit, the cross-sectional area of the proximal end of the diverging portion of the conduit is greater than the cross-sectional area of the distal end of the conduit. For some application, the divergence of the conduit along the diverging portion of the conduit is at a constant angle alpha (FIG. 1A) along the length of the diverging portion of the conduit, for example, such that the diverging portion of the conduit defines a frustoconical shape, as shown. For some applications, the angle of the divergence of the conduit along the diverging portion of the conduit changes along the length of the diverging portion of the conduit. For example, the angle of the divergence may increase from the proximal end of the portion to the distal end of the portion, such that inner surface 24 has a convex cross-section along the diverging portion of the conduit. For some applications, the diverging portion of the conduit defines a stratford ramp shape. Typically, the proximal and distal ends of the diverging portion of the conduit define circular cross-sections. Alternatively, the proximal and distal ends of the diverging portion of the conduit define elliptical cross-sections, polygonal cross-sections, or differently shaped cross-sections.

Typically, the angle of divergence alpha (which is measured with respect to a line 29 that is parallel to the longitudinal axis of the conduit, as shown in FIG. 1A), or the average angle of divergence, in cases in which the divergence varies along the length of the conduit, is greater than 1 degree (e.g., greater than 5 degrees, and less than 30 degrees (e.g., less than 20 degrees), e.g., 1-30 degrees, or 5-20 degrees.

Figure 2A:
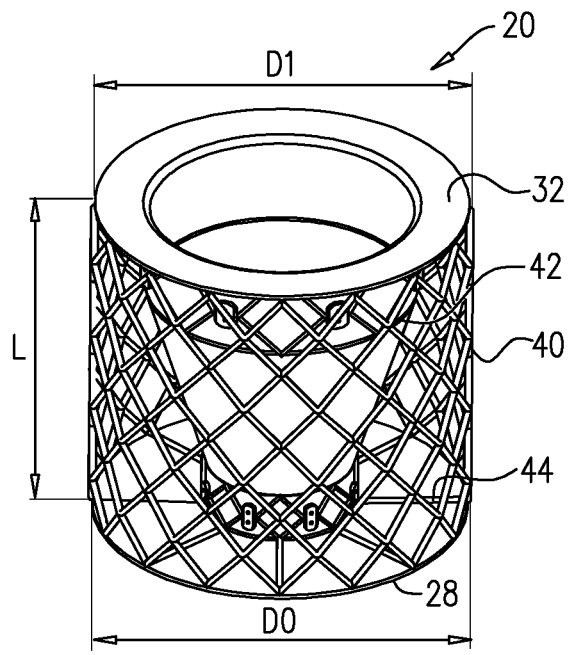
FIGS. 2A-C are schematic illustrations of a device for implanting inside a blood vessel of a subject, in accordance with some applications of the present invention.
Figure 2B:
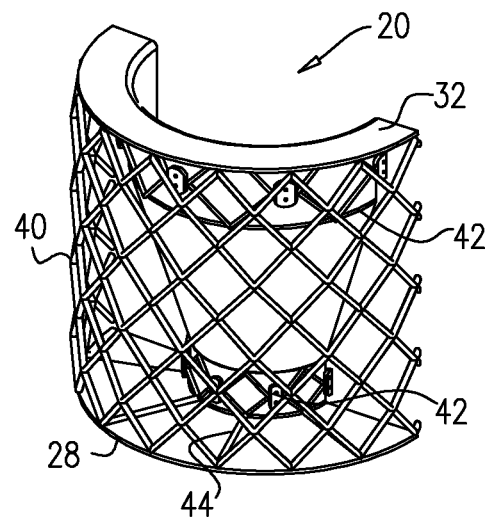
Figure 2C:
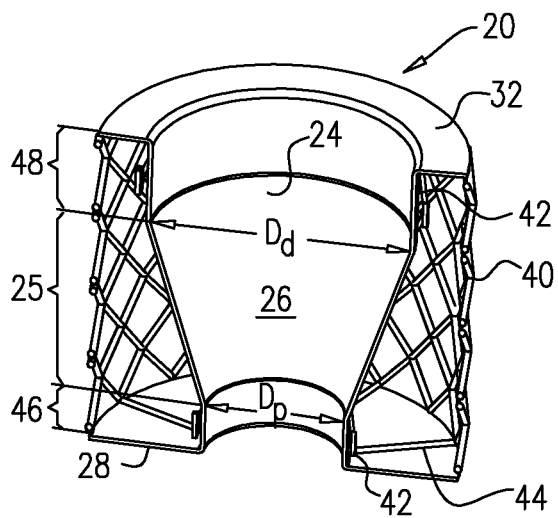

Reference is now made to FIGS. 2A-C, which are schematic illustrations of respective views of implantable device 20, in accordance with some applications of the present invention. As shown, for some applications, device 20 includes outer support structure 40. The outer support structure maintains device 20 within the blood vessel (e.g., the aorta) by contacting the inner wall of the blood vessel. For some applications, the outer support structure is a stent-like structure, the outer support structure being shaped as a cylindrical stent, and/or the support structure including struts of a metal or alloy, such as stainless steel or nitinol. When device 20 is deployed inside the subject's ascending aorta, the outer support structure anchors the device within the ascending aorta, by expanding such as to exert an outward radial force upon the inner wall of the aorta. For some applications, the outer support structure is configured such that an interface between the outer support structure and the inner wall of the blood vessel is sealed. For example, the outer support structure may be at least partially covered with a cover that seals the interface between the outer support structure and the inner wall of the blood vessel (e.g. cover 62, shown in FIG. 4B). For some applications, a different portion of the device is configured to form a seal between the device and the inner wall of the blood vessel, such that there is substantially no blood flow between the device and the inner wall of the blood vessel.

Typically, inner surface 24 is made of a flexible material that has low permeability (e.g., as described herein), such as expanded polytetrafluoroethylene (ePTFE) or woven polyester. The inner surface is supported by an inner support structure 42, which typically comprises struts of a metal or alloy, such as stainless steel or nitinol. For some applications, inner support structure and outer support structure are coupled to each other via rigid coupling elements 44, such as struts, as shown. Typically, coupling elements 44 also support proximal outer surface 28 and distal outer surface 32. For some applications, the proximal and distal outer surfaces are made of a similar material to that of inner surface 24. For some applications, inner surface 24, proximal outer surface 28, and/or distal outer surface 32 are made of a single continuous piece of material. Alternatively or additionally, inner surface 24, proximal outer surface 28, and/or distal outer surface 32 are formed separately from one another and are coupled to one another such that any interfaces between the surfaces are substantially sealed.

In general, device 20 as described with respect to any of the applications of the present invention may include any combination of modularly-formed components (i.e., components that are formed separately from one another) which are subsequently coupled to one another. Typically the modularly-formed components are coupled to one another such that any interfaces between the components are substantially sealed.

Typically, proximal outer surface 28 extends radially outward from the edge of the layer of material that defines inner surface 24 to the inner surface of outer support structure 40. Similarly, for applications, in which device 20 includes distal outer surface 32, the distal outer surface extends radially outward from the edge of the layer of material that defines inner surface 24 to the inner surface of the outer support structure. For some applications, the distal end of the inner surface extends radially outward to the inner wall of the blood vessel, and/or to the inner surface of the outer support structure, which is contact with the inner wall of the blood vessel, e.g., in the manner described with reference to FIGS. 6A-E, such that the distal end of the inner surface impedes blood flow around the outside of the distal end of the conduit.

For some applications, inner surface 24 that defines conduit 26 is rough. The rough surface of the conduit is configured to act as a turbulator on the boundary layer between the blood and the surface of the conduit, such as to increase adhesion, excite the boundary layer, and delay flow separation.

Typically, device 20 is inserted into the subject's ascending aorta via a catheter. In order to deploy the device inside the ascending aorta, the catheter is retracted, in response to which the device is configured to self-expand. For some applications, during the self-expansion of the device, the device traps blood between the inner wall of the aorta, conduit 26, proximal outer surface 28, and distal outer surface 32. For some applications, techniques are applied in order to cause the trapped blood to coagulate. For example, coil compaction techniques may be applied in order to cause the blood to coagulate. For some applications, device 20 is a balloon-expandable device that is configured to be expanded inside the ascending aorta by a balloon being inflated inside the device.

With reference to FIG. 2A, it is noted that, typically, length L of device 20 is greater than 20 mm (e.g., greater than 30 mm), and/or less than 70 mm (e.g., less than 60 mm), e.g., 20-70 mm, or 30-60 mm. For some applications, a ratio of (a) an diameter D0 of a proximal end of outer support structure 40 to (b) an outer diameter D1 of the distal end of the outer support structure is greater than 3:4, and/or less than 4:3, e.g., between 3:4 and 4:3. Outer diameter D0 of the proximal end of the outer support structure is typically made to conform with the inner diameter of the subject's aorta toward the proximal end of the device, and outer diameter D1 of the distal end of the outer support structure is typically made to conform with the inner diameter of the subject's aorta at the distal end of the device. Since there is some variation in the shapes and sizes of subject's aortas, the ratio of D0:D1 typically varies between 3:4 and 4:3. Typically, the maximum outer diameter of the device (i.e., the outer diameter of the device at the location along the length of the device at which the outer diameter is at its maximum) is greater than 18 mm (e.g., greater than 25 mm), and/or less than 45 mm (e.g., less than 35 mm), e.g., 18-45 mm, or 25-35 mm.

Further typically, with reference to FIG. 2C, it is noted that the difference between a proximal inner diameter Dp of conduit 26 at the proximal end of diverging portion 25 of the conduit, and a distal inner diameter Dd of conduit 26 at the distal end of the diverging portion of the conduit is greater than 3 mm (e.g., greater than 5 mm, or greater than 10 mm), and/or less than 30 mm (e.g., less than 20 mm), e.g., 5-30 mm, or 10-20 mm Typically, proximal inner diameter Dp is greater than 7 mm, and/or less than 14 mm, e.g., 7-14 mm. Further typically, distal inner diameter is greater than 12 mm and/or less than 44 mm, e g 12-44 mm.

For some applications, the ratio of diameter Dd of conduit 26 at the distal end of diverging portion 25 of the conduit to diameter Dp of the conduit at the proximal end of the diverging portion of the conduit is greater than 4:3 (e.g., greater than 2:1), and/or less than 4:1 (e.g., less than 3:1), e.g., 4:3-4:1, or 2:1-3:1. It is noted that the cross-section of the conduit is not necessarily circular. For applications in which the term "diameter" is used with reference to an object or a portion of an object having a non-circular cross-section, the term "diameter" should be interpreted as meaning the hydraulic diameter, i.e. 4 A/P (where A is the cross-sectional area, and P is the perimeter).

It is noted that, typically, the dimensions of device 20 described herein are the dimensions that the device is configured to have, when the device is in a non-constrained state. Typically, if the device is inserted via an insertion catheter, the device is constrained during its insertion, such that the dimensions of the device during the insertion may not be as described herein. However, when the device is in a deployed state inside a blood vessel of the subject (e.g., inside the subject's ascending aorta), the device is typically configured to have dimensions as described herein, since, when deployed inside the blood vessel, the device assumes its "non-constrained" configuration. It is further noted that, for some applications the device is implanted in a non-minimally-invasive manner (e.g., using traditional surgical techniques). For some such applications, even during the insertion of the device, the device is configured in its non-constrained state.

Figure 10A:
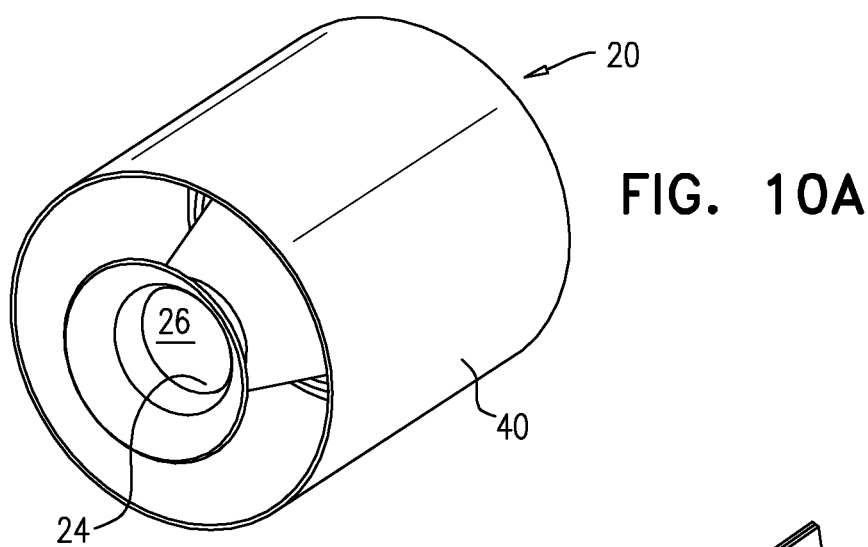
FIGS. 10A-C are schematic illustrations of a device for implanting inside a blood vessel of a subject, in accordance with some applications of the present invention.

With reference to FIG. 2C, it is noted that, for some applications, conduit 26 defines a proximal portion 46 that is disposed proximally to diverging portion 25, and/or a distal portion 48 that is distal to diverging portion 25. For some applications, as shown, proximal portion and/or distal portion have cylindrical shapes. Alternatively or additionally, proximal portion and/or distal portion may have a different shape. For example, one or both of the portions may have an elliptical cross-section along a plane that is perpendicular to the longitudinal axis of the conduit. For some applications, the proximal portion converges in the proximal to distal direction in order to direct blood from the aortic valve to diverging portion 25 of the conduit, e.g., as shown in FIG. 10A. For some applications, the distal portion is shaped such that when device 20 is disposed inside the ascending aorta, the distal portion curves toward the aortic arch, such that blood is directed toward the aortic arch.

As shown in FIG. 2C, for some applications, the proximal end of conduit 26 is level with the proximal end of outer support structure 40, such that surface 28, which surrounds the proximal end of the conduit and extends to the proximal end of the outer support structure, defines a flat disc shape. However, for some applications (not shown), the proximal end of the conduit extends in the proximal direction beyond the proximal end of the outer support structure. Alternatively, the proximal end of the outer support structure extends in the proximal direction beyond the proximal end of the conduit. For such applications, surface 28 is typically disposed at an angle with respect to a plane that is perpendicular to the longitudinal axis of the conduit. For some applications, surface 28 is curved. For example, the surface may be concave or convex, as described hereinbelow with reference to FIG. 10C.

Similarly, as shown in FIG. 2C, for some applications, the distal end of conduit 26 is level with the distal end of outer support structure 40, such that surface 32, which surrounds the distal end of the conduit and extends to the distal end of the outer support structure, defines a flat disc shape. However, for some applications (not shown), the distal end of the conduit extends in the distal direction beyond the distal end of the outer support structure. Alternatively, the distal end of the outer support structure extends in the distal direction beyond the distal end of the conduit. For such applications, surface 32 is typically disposed at an angle with respect to a plane that is perpendicular to the longitudinal axis of the conduit. For some applications, surface 32 is curved. For example, the surface may be concave or convex. As noted hereinabove, for some applications, the device does not define a separate distal outer surface. Rather, the distal end of the inner surface that defines the conduit extends to the inner wall of the blood vessel, and/or to the outer support structure, which is in contact with the inner wall of the blood vessel, such that the distal end of the inner surface impedes the backflow of blood around the outside of the distal end of the conduit, as shown in FIGS. 6A-E.

Figure 3:
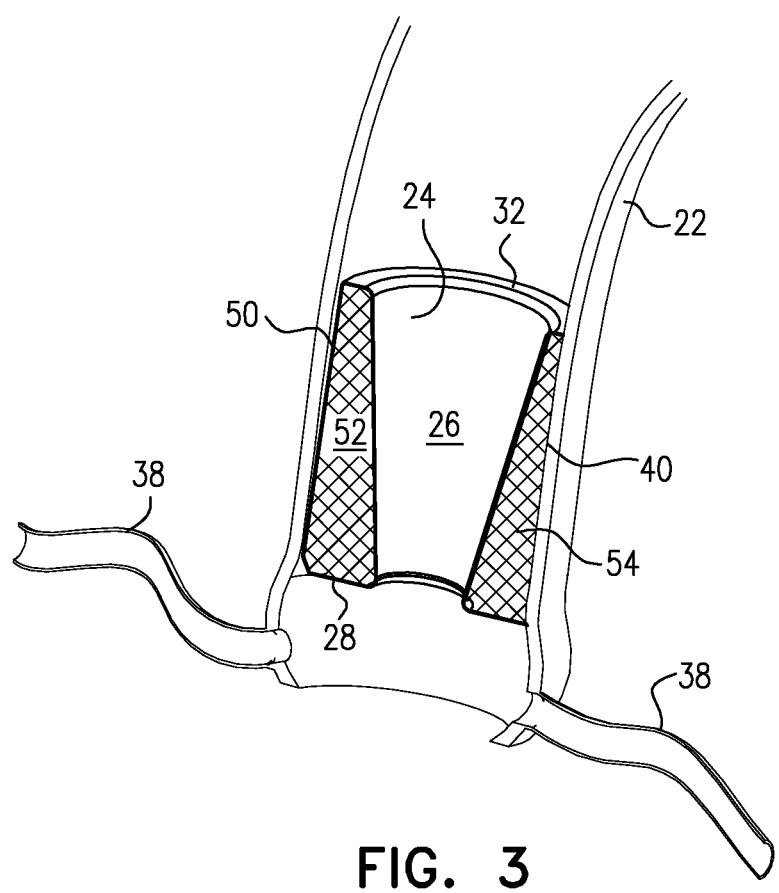
FIG. 3 is a schematic illustration of an implantable device deployed inside a subject's ascending aorta, in accordance with some applications of the present invention.

Reference is now made to FIG. 3, which is a schematic illustration of device 20 deployed inside a subject's aorta, in accordance with some applications of the present invention. Device 20 as shown in FIG. 3 is generally similar to device 20 described with reference to FIGS. 1A-2C, except for the differences described hereinbelow. For some applications, outer support structure 40 includes a material 50 having low permeability (e.g., as described hereinabove), such as expanded polytetrafluoroethylene (ePTFE) or woven polyester, such that a volume 52 between conduit 26, the ends of device 20, and the outer support structure is substantially sealed. For some such applications, subsequent to the deployment of device 20 inside the subject ascending aorta a filling material 54 (e.g., a biocompatible glue or self-solidifying gel) is injected into volume 52 such as to fill the volume. For some applications, the outer support structure includes a stent-like structure as described hereinabove, and includes material 50 on the inner or outer surface of the stent-like structure. Alternatively, the outer support structure may include material 50 and not include any rigid support elements. For such applications, the outer surface anchors device 20 to the ascending aorta by becoming radially expanded by virtue of filling material 54 being injected into volume 52.

Figure 4A:
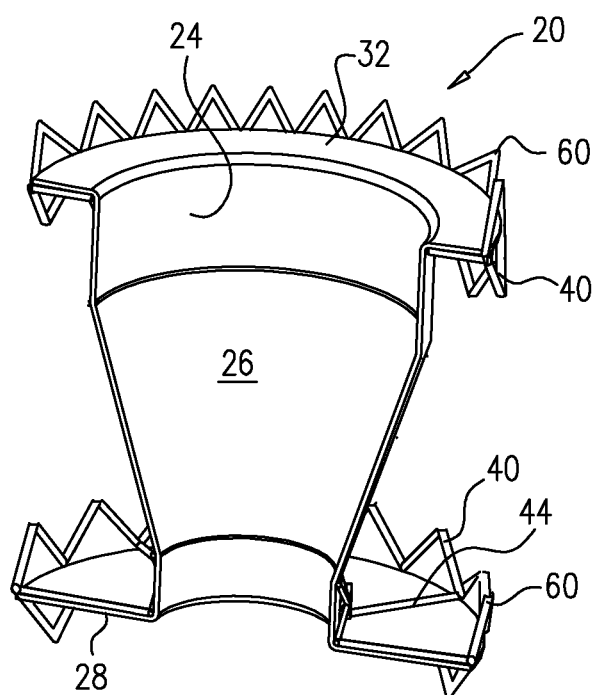
FIGS. 4A-B are schematic illustrations of a device for implanting inside a blood vessel of a subject, in accordance with some applications of the present invention.
Figure 4B:
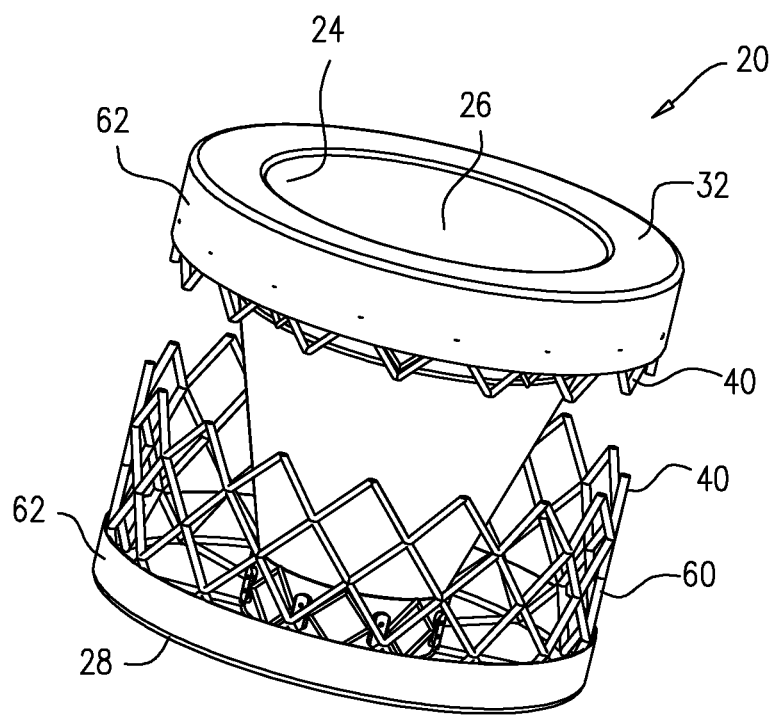

Reference is now made to FIGS. 4A-B, which are schematic illustrations of implantable device 20, in accordance with some applications of the present invention. Device 20 as shown in FIGS. 4A-B is generally similar to device 20 described with reference to FIGS. 1A-2C, except for the differences described hereinbelow. Outer support structure 40 of device 20 as shown in FIGS. 4A-B is not a continuous stent-like cylindrical structure. Rather, the outer support structure of device 20 as shown in FIGS. 4A-B include proximal and distal rings 60 of struts that are configured to anchor, respectively, the proximal and distal ends of device 20 to the subject's ascending aorta, by radially expanding such as to exert an outward radial force upon the inner wall of the ascending aorta. It is noted that, as shown in FIG. 4A and FIG. 4B, the proximal and distal rings of struts may have different lengths and/or shapes from one another. For some applications, the strut rings extend both proximally and distally with respect to the proximal and distal surfaces, as shown in FIG. 4A. Alternatively, the proximal ring of struts may only extend distally with respect to proximal surface, and the distal strut ring may only extend proximally with respect to the distal outer surface, as shown in FIG. 4B. For some applications, the strut rings or portions thereof are covered with a cover 62, such as expanded polytetrafluoroethylene (ePTFE) or woven polyester, as shown in FIG. 4B. Typically, the cover is made of a similar material to that of inner surface 24, proximal outer surface 28, and distal outer surface 32. Further typically, cover 62 seals the interface between the outer support structure and the inner wall of the blood vessel.

Figure 5A:
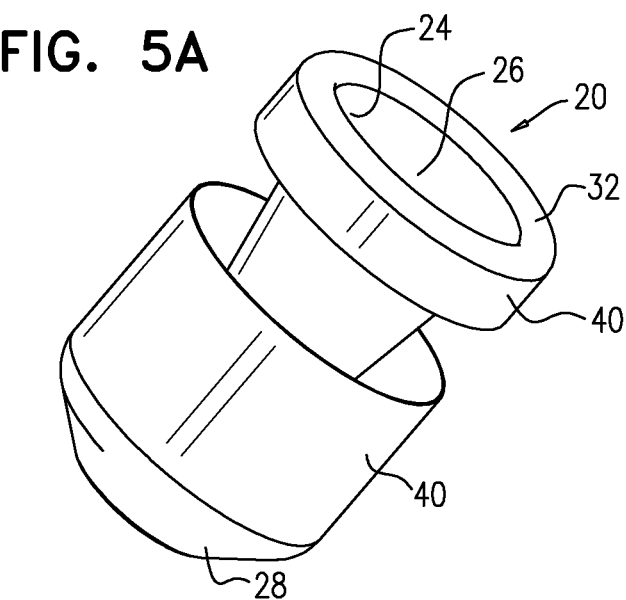
FIGS. 5A-C are schematic illustrations of respective views of a device for implanting inside a blood vessel of a subject, in accordance with some applications of the present invention.
Figure 5B:
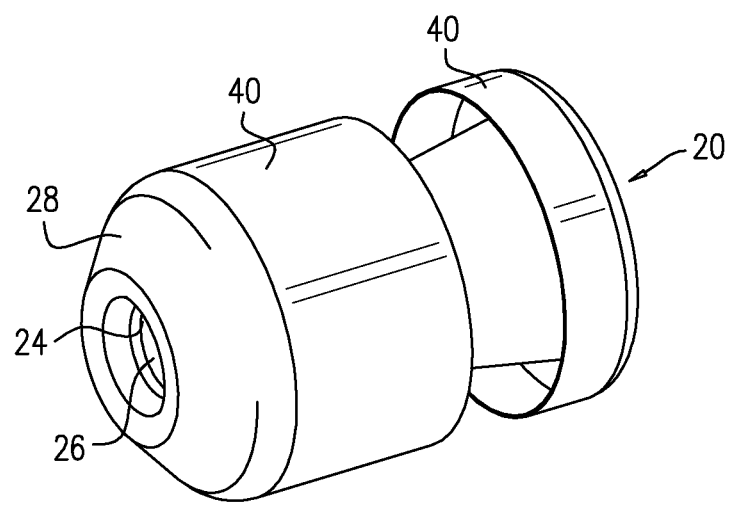
Figure 5C:
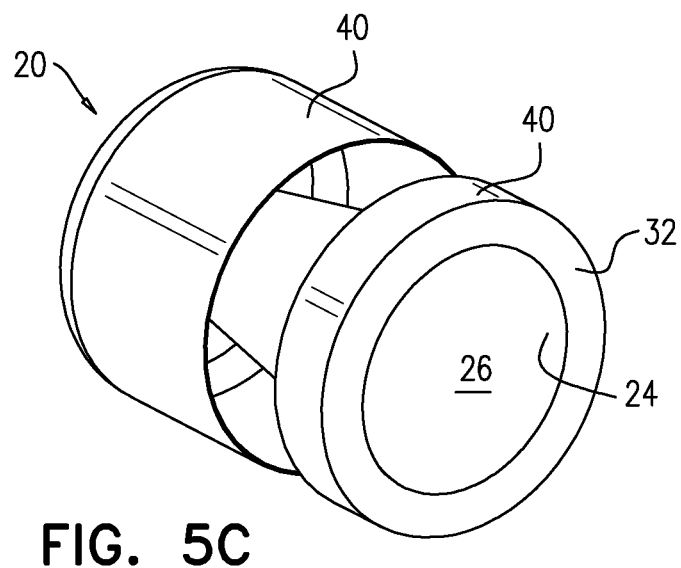

Reference is now made to FIGS. 5A-C, which are schematic illustrations of device 20, the device being made of stent graft material, in accordance with some applications of the present invention. FIGS. 5A-C show respective three-dimensional views of the device. Device 20 as shown in FIGS. 5A-C is generally similar to device 20 as shown in FIG. 4B except for the differences described hereinbelow.

For some applications, inner surface 24, proximal outer surface 28, distal outer surface 32, and outer support structure 40 are all formed of a single continuous portion of graft material. The graft material is typically formed from a combination of a metal or alloy stent (e.g., a stent made of stainless steel or nitinol) and fabric (such as expanded polytetrafluoroethylene (ePTFE) or woven polyester). FIGS. 5A-C shows the device having a generally similar shape to that shown in FIG. 4B, i.e., with the device defining a distal outer surface 32, and with the outer support structure not being continuous along the length of the device, but including support rings that are disposed distally to the proximal outer surface and proximally to the distal outer surface. However, the scope of the present invention includes using a continuous portion of graft material to form a device having any one of the other structures described herein. For example, the graft material could be used to form a device that does not define a distal outer surface, but which defines an inner surface that extends to the inner wall of the blood vessel (as shown in FIGS. 6A-E). Or, the graft material could be used to form a device having an outer support structure that runs continuously along the length of the device (e.g., as shown in FIGS. 1A-3). For some applications, graft material is used to form device 20, but the device is not formed from a single portion of graft material. Rather, the device may be formed from a plurality of pieces of graft material that are coupled to each other.

Figure 6A:
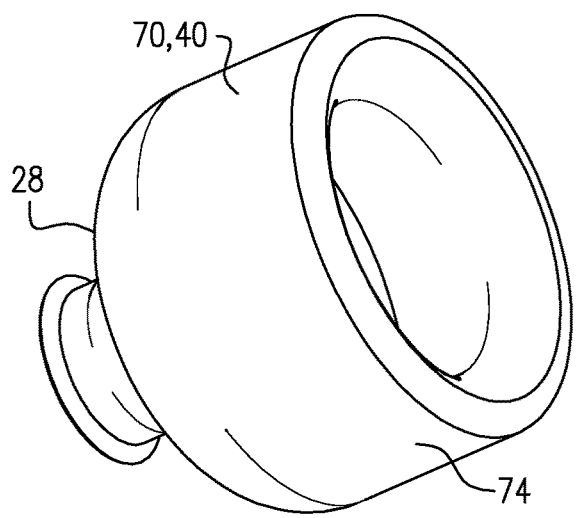
FIGS. 6A-E are schematic illustrations of a device for implanting inside a blood vessel of a subject, and components of the device, in accordance with some applications of the present invention.
Figure 6B:
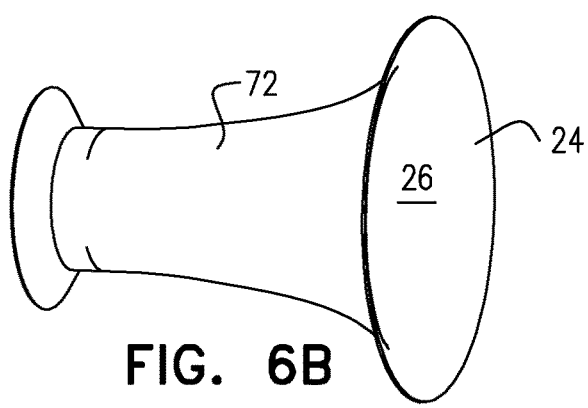
Figure 6C:
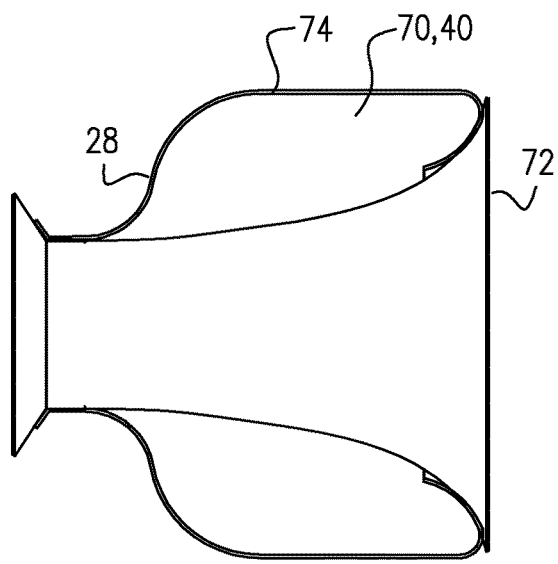
Figure 6D:
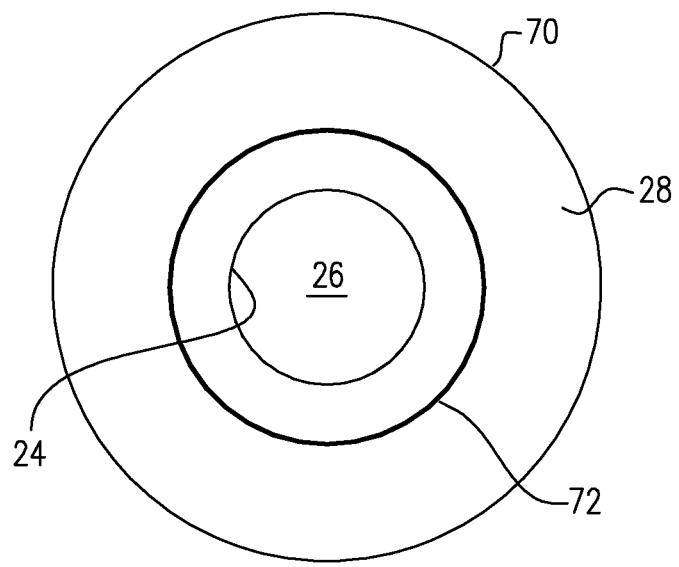
Figure 6E:
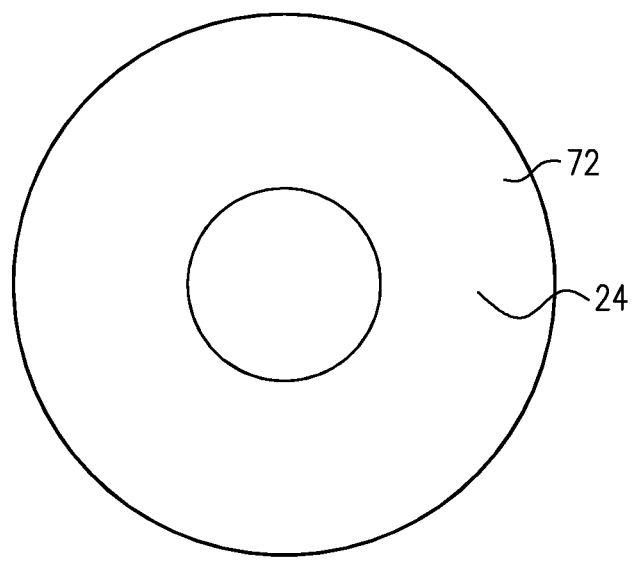

Reference is now made to FIGS. 6A-E, which are schematic illustrations of components of device 20, for implanting inside a blood vessel of a subject (e.g., the subject's ascending aorta, as described hereinabove), in accordance with some applications of the present invention. For some applications, device 20 includes an outer stent 70 and an inner structure 72 that defines conduit 26. FIG. 6A shows outer stent 70, FIG. 6B shows inner structure 72, and FIGS. 6C-E show respective views of the inner structure disposed inside the outer stent, in the manner in which the inner structure and outer stent are typically deployed inside the subject's blood vessel (e.g., inside the subject's ascending aorta).

Outer stent is configured to anchor device 20 within the ascending aorta, by outer surface 74 of the stent exerting a radial force upon the inner wall of the aorta. In this regard, outer surface 74 functions as outer support structure 40, as described hereinabove. In accordance with respective applications, the outer stent is self-expandable, or is balloon-expandable. Inner structure is configured to be disposed inside the outer stent and for the inner surface of the inner structure to define conduit 26. In accordance with respective applications, the inner structure is self-expandable, or is balloon-expandable.

For some applications, the outer stent and the inner structure are inserted into the subject's ascending aorta simultaneously, with the inner structure already disposed inside the outer stent. For some applications, the outer stent and the inner structure are a single integrated structure, or are coupled to one another. Typically, for such applications, the outer stent and the inner structure are deployed in a single deployment step. For example, the outer stent and the inner structure may be allowed to self expand, or be expanded using a balloon, at the time as one another. Alternatively, the outer stent and the inner structure are inserted and/or deployed in separate insertion and/or deployment steps. For example, the outer stent may first be deployed (e.g., via self-expansion or via balloon expansion) inside the ascending aorta, such that the outer stent becomes anchored in position within the ascending aorta. Subsequently, the inner stent may be deployed (e.g., via self-expansion or via balloon expansion) inside the outer stent.

FIGS. 6C-E show respective views of the inner structure disposed inside the outer stent. FIG. 6Ci shows a lateral transparent view of the outer stent and the inner structure, and FIGS. 6D and 6E show, respectively, proximal and distal end views of the outer stent and the inner structure.

As may be observed in FIGS. 6C-6D, outer stent 70 defines proximal surface 28, which extends from outside conduit 26 to the portion of the outer stent that is contact with the inner wall of the blood vessel. The proximal surface is configured to substantially prevent antegrade blood flow around the outside of the conduit, for example, in order to reduce a likelihood of eddie currents and/or stagnated blood forming in the region surrounding the conduit. Typically, the proximal outer surface is disposed around conduit 26 such that at least a portion of the surface is at a longitudinal location that is within the proximal-most 30 percent of the length of the conduit.

As may be observed in FIGS. 6C and 6E, in accordance with some applications of the present invention, device 20 does not define a separate distal outer surface. Rather, the distal end of the inner surface that defines the conduit extends to the inner wall of the blood vessel, such that the distal end of the inner surface impedes the backflow of blood around the outside of the distal end of the conduit. Typically, the distal end of the inner surface impedes the backflow of blood around the outside of the distal end of the conduit in a generally similar manner to that described hereinabove with respect to the distal outer surface. For example, the inner surface may be impermeable, and/or may have a permeability per unit length of less than 0.25 micrometers (as described hereinabove). For some applications, the inner surface includes a material (such as a fabric, a metal, or an alloy) that is structured such that there are open spaces between portions of the material. For example, the material may be arranged in a lattice structure, a braided structure, a criss-cross structure, a woven structure, a cellular structure, a stitched structure, or a similar structure. Typically, even for such applications, more than 20 percent of the area of the inner surface is filled with material, and less than 80 percent of the area of the inner surface is open space between the material. Further typically, more than 50 percent, e.g., more than 80 percent, of the area of each of the inner surface is filled with material. For some applications, there are no open spaces within the inner surface (i.e., the entirety of the inner surface is filled with material).

Figure 7:
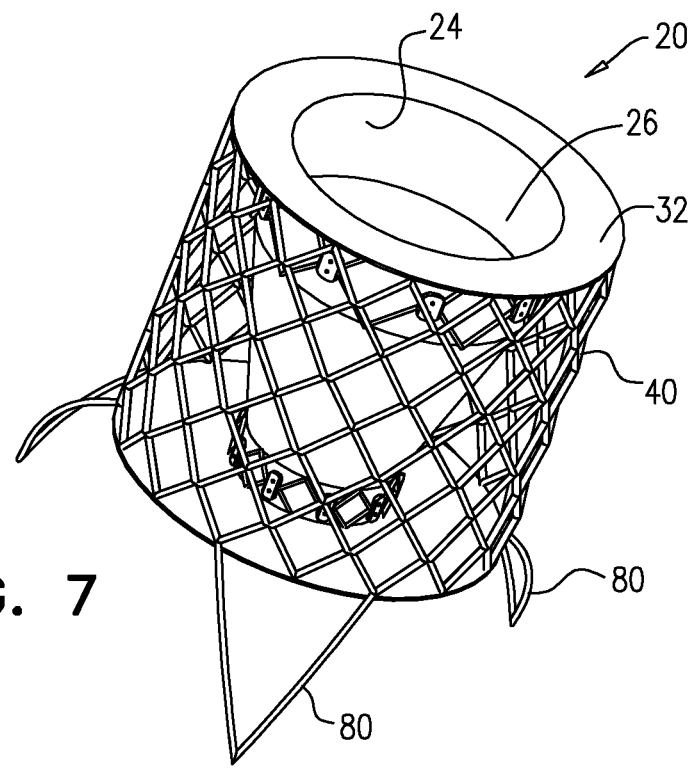
FIG. 7 is a schematic illustration of a device for implanting inside a blood vessel of a subject, in accordance with some applications of the present invention.

Reference is now made to FIG. 7, which is a schematic cross-sectional illustration of implantable device 20, in accordance with some applications of the present invention. Device 20 as shown in FIG. 7 is generally similar to device 20 described with reference to FIGS. 1A-2C, except for the differences described hereinbelow. For some applications, device 20 includes anchors 80 that extend from the proximal end of outer support structure 40. The anchors are curved such as to conform with the shapes of the aortic sinuses. The anchors are configured to become deployed within the aortic sinuses and to anchor device 20 within ascending aorta, by preventing downstream migration of the device.

Figure 8:
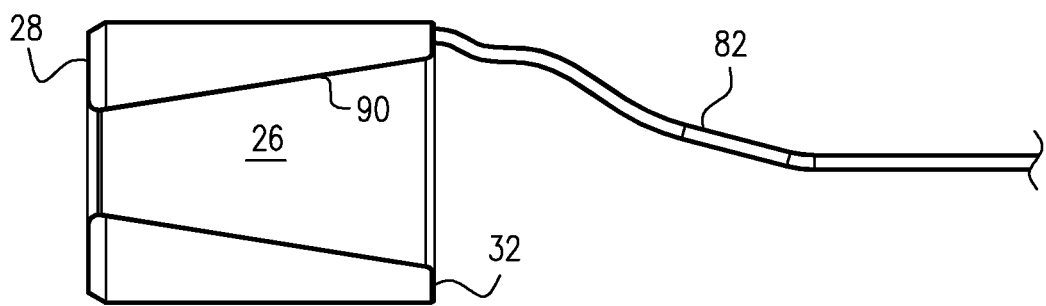
FIG. 8 is a schematic illustration of a device for placing inside a blood vessel of a subject, in order to regulate blood flow through the blood vessel, in accordance with some applications of the present invention.

Reference is now made to FIG. 8, which is a schematic illustration of device 20, device 20 being configured for placing inside a blood vessel of a subject, in order to regulate blood flow through the blood vessel, in accordance with some applications of the present invention. For some applications, device 20 includes a set of one or more balloons that is configured, upon being inflated, to define a surface 90 that provides longitudinal conduit 26 through the set of balloons, at least a portion of the conduit being shaped to diverge in a direction from the proximal end of the conduit to the distal end of the conduit, such that the cross-sectional area of the conduit at the downstream end is greater than the cross-sectional area of the conduit at the upstream end. The set of balloons is configured to be inflated inside a longitudinal portion of a blood vessel via an inflation lumen 82. The set of balloons defines proximal and distal outer surfaces 28, 32 configured to impede blood flow around the outside of the conduit. Upon being inflated inside the longitudinal portion of the blood vessel, the set of balloons prevents blood flow through the longitudinal portion via any flow paths other than through the conduit defined by surface 90, in a generally similar manner to that described hereinabove.

Typically, the set of balloons is inflated inside the ascending aorta of a subject suffering from aortic valve stenosis, in order to provide an acute treatment of symptoms associated with the stenosis, e.g., by decreasing the subject's left ventricular pressure, reducing afterload, and/or and improving cardiac output. The set of balloons is configured to treat the symptoms associated with the stenosis in a generally similar manner to that described hereinabove. For some applications, the set of balloons is used to apply an acute treatment to a subject. Typically, for such applications, the set of balloons is deflated and removed from the subject's body within less than one month (e.g., less than one week, or less than one day) after having been inflated inside the subject's ascending aorta. For some applications, the set of balloons is inflated inside the subject's aorta, and remains implanted inside the aorta, in order to provide chronic treatment to the subject. Typically, subsequent to inflating the balloons, inflation lumen is removed from the subject's body.

Figure 9A:
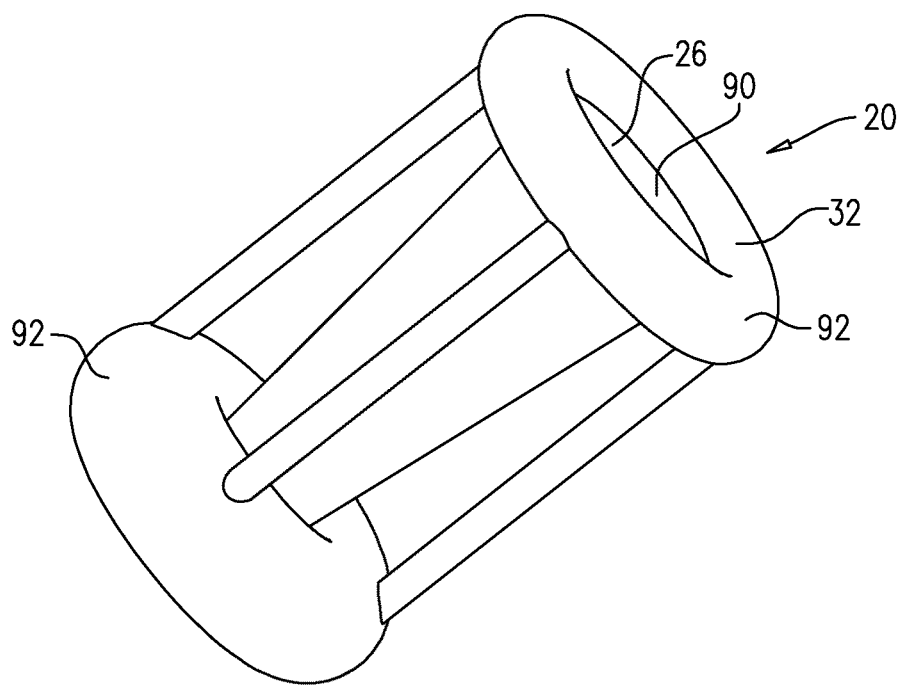
FIGS. 9A-B are schematic illustrations of respective views of a device for placing inside a blood vessel of a subject, in order to regulate blood flow through the blood vessel, in accordance with some applications of the present invention.
Figure 9B:
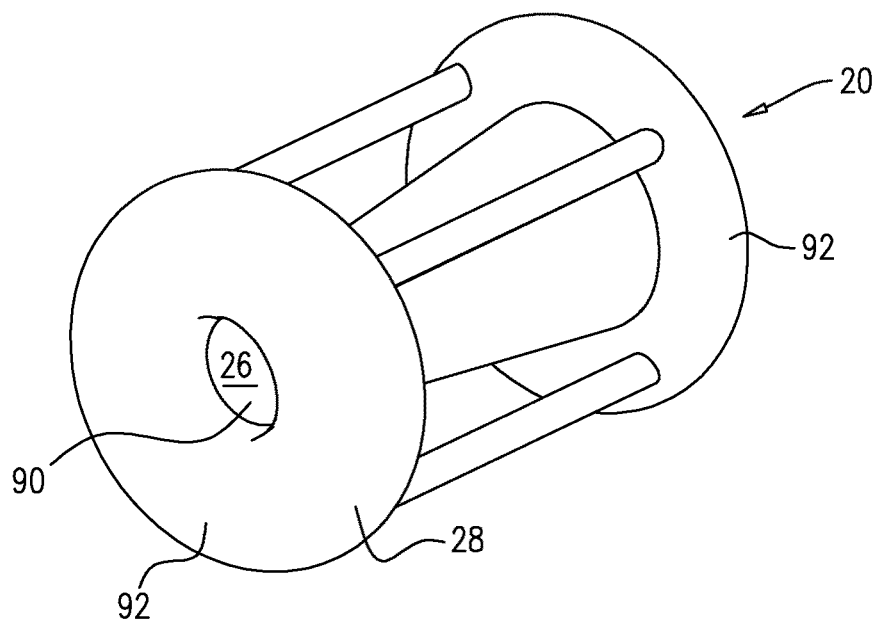

Reference is now made to FIGS. 9A-B, which are schematic illustrations of respective views of device 20, device 20 being configured for placing inside a blood vessel of a subject, in order to regulate blood flow through the blood vessel, in accordance with some applications of the present invention. As shown, for some applications, device 20 includes a set of one or more balloons that is configured, upon being inflated, to define a surface 90 that defines a longitudinal conduit through the set of balloons, at least a portion of the conduit being shaped to diverge in a direction from the proximal end of the conduit to the distal end of the conduit, such that the cross-sectional area of the conduit at the downstream end is greater than the cross-sectional area of the conduit at the upstream end. The set of balloons also defines proximal and distal toroidal portions 92 that are disposed, respectively around the proximal and distal ends of the conduit. The toroidal portions define proximal and distal outer surfaces 28, 32. The set of balloons is configured to be inflated inside a longitudinal portion of a blood vessel. Upon being inflated inside the longitudinal portion of the blood vessel, the proximal and distal outer surfaces of the toroidal portions of the balloon are configured to impede blood flow through the longitudinal portion via any flow paths other than through the conduit defined by surface 90, in a generally similar manner to that described hereinabove.

It is noted with respect to FIG. 8 and FIGS. 9A-B that, for some applications, the compliance of respective portions of the set of balloons may differ from one another in a manner that facilitates the flow of blood through the conduit defined by device 20 in a desired manner.

Figure 10B:
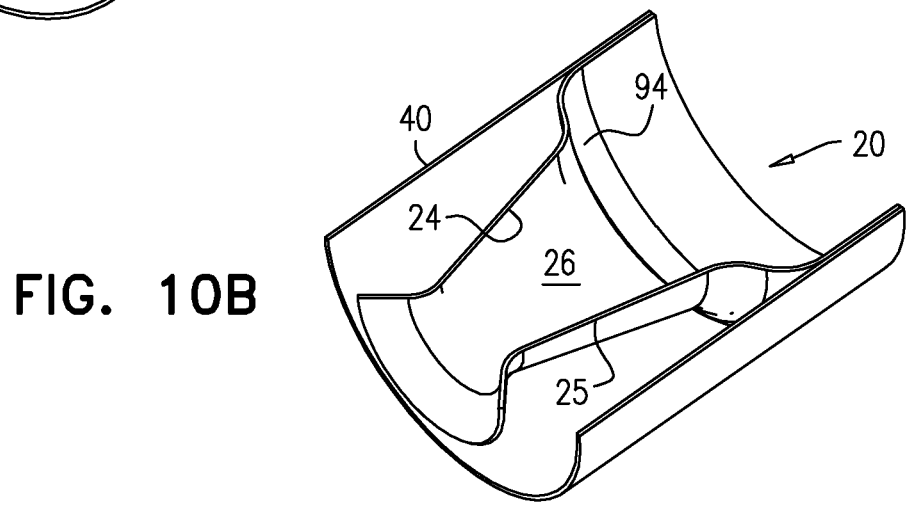
Figure 10C:
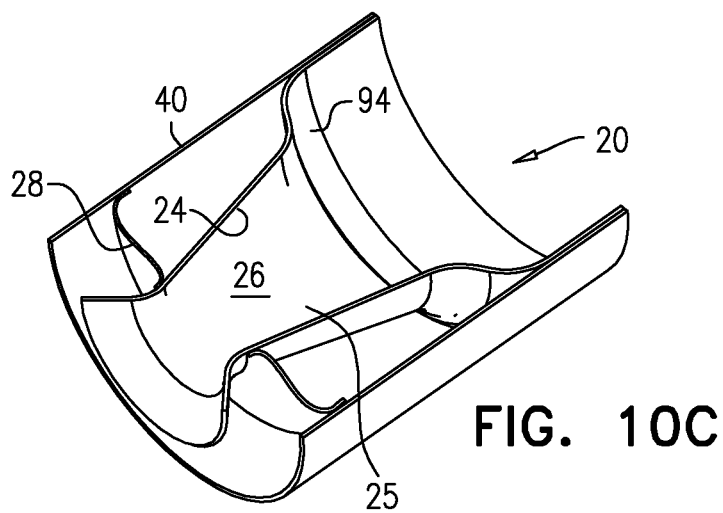

Reference is now made to FIGS. 10A-C, which are schematic illustrations of device 20, in accordance with some applications of the present invention. As described with reference to FIGS. 5A-C, device 20 as shown in FIGS. 10A-C is made of stent graft material, in accordance with some applications of the present invention. The stent graft material defines outer support structure 40, which contacts the inner wall of the blood vessel, as well as inner surface 24, which defines conduit 26.

FIG. 10A shows a three-dimensional view of device 20, and FIGS. 10B-C show cross-sectional views of device 20, in accordance with respective embodiments, the cross-sectional views being taken along the longitudinal axis of the device. As shown in FIGS. 10A-C, for some applications, at the distal end of inner surface 24 (which defines conduit 26), a surface 94, which is concavely curved in the downstream direction, extends to the inner surface of the outer support structure 40. The concavely curved surface is continuous with inner surface 24. As such, the concavely curved surface may alternatively be viewed as a continuation of the distal end of the inner surface, or as a distal outer surface which extends from the inner surface to the outer support structure. Regardless of how the concavely-curved surface is viewed (a continuation of inner surface 24, or as a distal outer surface), device 20 defines, at its distal end, a surface that extends radially outward, around the full circumference of the conduit, from the conduit at least to the radial location of the inner surface of the outer support structure (such that the surface extends to the inner surface of the blood vessel, and/or to the outer support structure). One of the functions of the surface is to substantially impede backflow of blood around the outside of conduit 26, as described hereinabove. In general, the scope of the present invention includes using any form of surface that extends radially outward, around the full circumference of the conduit, from the conduit at least to the radial location of the inner surface of the outer support structure (such that the surface extends to the inner surface of the blood vessel, and/or to the outer support structure), and that is configured to impede backflow of blood around the outside of the distal end of conduit 26, in the manner described herein.

As shown in FIGS. 10A-C, and as described hereinabove, for some applications, at the proximal end of conduit 26, inner surface 24 converges in the proximal to distal direction in order to direct blood from the aortic valve to diverging portion 25 of the conduit.

It is noted with reference to FIG. 10B that, for some applications, device 20 does not define a proximal outer surface that extends radially outward, around the full circumference of the conduit, from the conduit at least to the radial location of the inner surface of the outer support structure, and at least a portion which is within a proximal-most 30 percent of a length of the conduit. Alternatively, as shown in FIG. 10C, for some applications device 20 does define a proximal outer surface that extends radially outward, around the full circumference of the conduit, from the conduit at least to the radial location of the inner surface of the outer support structure, and at least a portion which is within a proximal-most 30 percent of a length of the conduit, as described hereinabove. For some applications, the proximal outer surface is curved, as shown in FIG. 10C. As described hereinabove, typically, the proximal outer surface is disposed around conduit 26 such that at least a portion of the surface is at a longitudinal location that is within the proximal-most 30 percent of the length of the conduit. For some applications, the proximal outer surface is configured to impede antegrade blood flow around the outside of conduit 26, for example, in order to reduce a likelihood of eddie currents and/or stagnated blood forming in the region surrounding the conduit.

EXPERIMENTAL DESCRIPTION

Experiments were conducted in which models were constructed in order to at least partially replicate the conditions of blood flow from a subject's left ventricle to the ascending aorta, via a stenosed aortic valve. An acrylic nozzle that defined an opening of 10 mm was inserted into a silicone tube having a diameter of 35 mm, and fluid was pumped through the tube, via the nozzle. Both water and a glycerin solution (which has a viscosity that is similar to that of blood) were used as the fluid. The flow of fluid through the nozzle and into the tube downstream of the nozzle replicates blood flow through a stenosed aortic valve into the ascending aorta, inasmuch as there is a flow of fluid through a relatively small opening into a lumen having a substantially larger diameter. The pressure inside the tube upstream of the nozzle replicates pressure in the left ventricle upstream of the aortic valve.

Devices as described herein were placed inside the tube downstream of the nozzle (i.e., the location representing the ascending aorta) and changes in pressure upstream of the nozzle (i.e., the location representing the left ventricle) were measured. It was found that in certain cases placing the devices downstream of the nozzle reduced pressure inside the tube upstream of the nozzle by up to 60 percent.

For example, in one case, a device made of solid acrylic, and having a generally similar shape to that of device 20 as shown in FIG. 3 of the present application, was placed such that the proximal end of the device was 1 mm from the end of the nozzle. The inner diameter of the conduit at the proximal end of the device was 10 mm, the inner diameter of the conduit at the distal end of the device was 20 mm, and the device had a length of 5 cm. Placement of the device in the above-described manner resulted in a 60 percent reduction in the pressure inside the tube upstream of the nozzle.

In another case, a device made of solid acrylic, and having a generally similar shape to that of device 20 as shown in FIG. 6C of the present application, was placed such that the proximal end of the device was 9 mm from the end of the nozzle. The inner diameter of the conduit at the proximal end of the device was 10 mm, the inner diameter of the conduit at the distal end of the device was 28 mm, and the device had a length of 3.5 cm. Placement of the device in the above-described manner resulted in a 40 percent reduction in the pressure inside the tube upstream of the nozzle.

The above results indicate that placement of devices as described herein inside the ascending aorta of a subject suffering from aortic valve stenosis may result in a decrease in the subject's left ventricular pressure.

It is noted that, although device 20 is generally described herein as being implanted in the subject's ascending aorta, the scope of the present invention includes placing device 20 inside a longitudinal portion of any blood vessel of a subject, such that the device causes blood to flow in an antegrade direction through conduit 26, and such that, within the longitudinal portion in which the device is placed, blood flow via any flow-path other than through the conduit is prevented by the deployment of the device within the portion.

The terms "proximal" and "distal" as used in the present application refer to the location of the respective elements in the aorta with respect to the aortic valve. That is, the term "proximal" refers to an element that is "upstream" and closer to the aortic valve, and the term "distal" refers to an element that is "downstream" and further from the aortic valve. Thus, the term "proximal" is used synonymously with the term "upstream" and the term "distal" is used synonymously with the term "downstream." In cases in which the device is placed in a different position within the subject's body, the terms "proximal" and "distal" are to be understood with respect to the direction of blood flow, a location that is relatively upstream being considered "proximal" and a location that is relatively downstream being considered "distal."

There is therefore provided the following inventive concepts, in accordance with some applications of the present invention:

Inventive concept 1. A method for regulating blood flow in an ascending aorta of a subject, the method comprising:

inserting, into the ascending aorta, a device that, when in a deployed state, defines an inner surface that defines a conduit through the device from an upstream end of the device to a downstream end of the device, at least a portion of the inner surface diverging in a direction from an upstream end of the diverging portion to a downstream end of the diverging portion, such that a cross-sectional area of the conduit at the downstream end of the diverging portion is greater than the cross-sectional area of the conduit at the upstream end of the diverging portion; and deploying the device within the ascending aorta such that an outer support structure of the device comes into contact with an inner wall of the aorta, and such that backflow of blood between a distal end of the inner surface and the outer support structure is impeded.

Inventive concept 2. The method according to inventive concept 1, wherein the device does not include a prosthetic valve, and wherein inserting the device into the ascending aorta does not include inserting a prosthetic valve into the ascending aorta.

Inventive concept 3. The method according to inventive concept 1, wherein inserting the device into the ascending aorta comprises inserting the device into the ascending aorta, a portion of the inner surface that is proximal to the diverging portion of the conduit, defining a converging portion of the conduit that converges in a direction from an upstream end of the converging portion to a downstream end of the converging portion.

Inventive concept 4. The method according to inventive concept 1, wherein the device includes a set of one or more balloons, and wherein deploying the device comprises inflating the one or more balloons.

Inventive concept 5. The method according to inventive concept 1, further comprising identifying the subject as suffering from an aortic valve stenosis, and wherein deploying the device comprises treating the subject by reducing pressure loss within the ascending aorta relative to pressure loss within the ascending aorta in an absence of the device.

Inventive concept 6. The method according to any one of inventive concepts 1-5, wherein inserting the device into the ascending aorta comprises inserting the device into the ascending aorta, the device having a length of more than 20 mm, when in the deployed state.

Inventive concept 7. The method according to inventive concept 6, wherein inserting the device into the ascending aorta comprises inserting the device into the ascending aorta, the length of the device being less than 70 mm.

Inventive concept 8. The method according to any one of inventive concepts 1-5, wherein inserting the device into the ascending aorta comprises inserting the device into the ascending aorta, a ratio of a diameter of the conduit at the downstream end of the diverging portion to a diameter of the conduit at the upstream end of the diverging portion being greater than 4:3, when the device is in the deployed state.

Inventive concept 9. The method according to inventive concept 8, wherein inserting the device into the ascending aorta comprises inserting the device into the ascending aorta, the ratio of the diameter of the conduit at the downstream end of the diverging portion to the diameter of the conduit at the upstream end of the diverging portion being greater than 2:1.

Inventive concept 10. The method according to inventive concept 8, wherein inserting the device into the ascending aorta comprises inserting the device into the ascending aorta, the ratio of the diameter of the conduit at the downstream end of the diverging portion to the diameter of the conduit at the upstream end of the diverging portion being less than 4:1.

Inventive concept 11. The method according to any one of inventive concepts 1-5, wherein inserting the device into the ascending aorta comprises inserting the device into the ascending aorta, a difference between a diameter of the conduit at the downstream end of the diverging portion to a diameter of the conduit at the upstream end of the diverging portion being greater than 3 mm, when the device is in the deployed state.

Inventive concept 12. The method according to inventive concept 11, wherein inserting the device into the ascending aorta comprises inserting the device into the ascending aorta, the difference between the diameter of the conduit at the downstream end of the diverging portion to the diameter of the conduit at the upstream end of the diverging portion being greater than 5 mm.

Inventive concept 13. The method according to inventive concept 11, wherein inserting the device into the ascending aorta comprises inserting the device into the ascending aorta, the difference between the diameter of the conduit at the downstream end of the diverging portion to the diameter of the conduit at the upstream end of the diverging portion being less than 30 mm.

Inventive concept 14. The method according to any one of inventive concepts 1-5, wherein inserting the device into the ascending aorta comprises inserting the device into the ascending aorta, the inner surface and the outer support structure being made of stent graft material.

Inventive concept 15. The method according to inventive concept 14, wherein inserting the device into the ascending aorta comprises inserting the device into the ascending aorta, the inner surface and the outer support structure being made of respective, separate pieces of stent graft material.

Inventive concept 16. The method according to inventive concept 14, wherein inserting the device into the ascending aorta comprises inserting the device into the ascending aorta, the inner surface and the outer support structure being made of a single continuous piece of stent graft material.

Inventive concept 17. The method according to any one of inventive concepts 1-5, wherein deploying the device within the longitudinal portion of the ascending aorta, such that such that backflow of blood between a distal end of the inner surface and the outer support structure is impeded comprises deploying the device such that a surface of the device extends radially outward around a full circumference of the conduit and contacts a location selected from the group consisting of: an inner wall of the aorta and the outer support structure, the surface being configured to impede blood flow therethrough.

Inventive concept 18. The method according to inventive concept 17, wherein deploying the device such that the surface of the device extends radially outward around the full circumference of the conduit and contacts the selected location comprises deploying the device such that a surface of the device that has a permeability per unit length of less than 0.25 micrometers extends radially outward around the full circumference of the conduit and contacts the selected location.

Inventive concept 19. The method according to inventive concept 17, wherein deploying the device such that the surface of the device extends radially outward around the full circumference of the conduit and contacts the selected location comprises deploying the device such that a downstream end of the inner surface that defines the conduit extends radially outward around the full circumference of the conduit and contacts the selected location.

Inventive concept 20. The method according to inventive concept 17, wherein deploying the device such that the surface of the device extends radially outward around the full circumference of the conduit and contacts the selected location comprises deploying the device such that a surface that is disposed around the full circumference of the conduit at the downstream end of the conduit and that extends radially outward contacts the selected location.

Inventive concept 21. The method according to inventive concept 17, wherein deploying the device such that the surface of the device extends radially outward around the full circumference of the conduit and contacts the selected location comprises deploying the device such that a surface extends radially outward and contacts the selected location, the surface being disposed around the full circumference of the conduit at a longitudinal location such that at least a portion of the surface is within a proximal-most 30 percent of a length of the conduit.

Inventive concept 22. The method according to inventive concept 17, wherein deploying the device within the longitudinal portion of the ascending aorta, such that backflow of blood between a distal end of the inner surface and the outer support structure is impeded comprises deploying the device such that two surfaces of the device extend radially outward around the full circumference of the conduit and contact the selected location, both of the surfaces being configured to impede blood flow therethrough.

Inventive concept 23. The method according to inventive concept 22, wherein deploying the device such that two surfaces of the device extend radially outward around the full circumference of the conduit and contact the selected location comprises causing blood to coagulate in a region between the two surfaces.

Inventive concept 24. The method according to inventive concept 22, further comprising injecting filling material into a region between the two surfaces.

Inventive concept 25. The method according to any one of inventive concepts 1-5, wherein deploying the device within the ascending aorta comprises deploying the device within a longitudinal portion of the ascending aorta, such that blood flow through the longitudinal portion of the ascending aorta, via any flow path other than through the conduit, is less than 20 percent of total blood flow through the longitudinal portion of the ascending aorta.

Inventive concept 26. The method according to inventive concept 25, wherein deploying the device within the longitudinal portion of the ascending aorta comprises deploying the device within the longitudinal portion of the ascending aorta such that there is no blood flow through the longitudinal portion of the aorta, via any flow path other than through the conduit.

Inventive concept 27. Apparatus comprising:
  an implantable device configured to be implanted inside a blood vessel of a subject, the device, when in a non-constrained configuration, being configured to define:
    an inner surface that defines a conduit through the device from a proximal end of the device to a distal end of the device, at least a portion of the inner surface diverging in a direction from a proximal end of the conduit to a distal end of the conduit, such that a ratio of a diameter of the conduit at a distal end of the diverging portion to a diameter of the conduit at a proximal end of the diverging portion is greater than 4:3; and
    an outer support structure configured to maintain the device inside the blood vessel by contacting the inner wall of the blood vessel,
    a ratio between an outer diameter of a proximal end of the outer support structure and an outer diameter of a distal end of the outer support structure being between 3:4 and 4:3.

Inventive concept 28. The apparatus according to inventive concept 27, wherein the implantable device does not include a prosthetic valve.

Inventive concept 29. The apparatus according to inventive concept 27, wherein the device is configured such that, upon the device being implanted within a longitudinal portion of an ascending aorta of the subject, the device reduces pressure loss within the ascending aorta relative to pressure loss within the ascending aorta in an absence of the device.

Inventive concept 30. The apparatus according to inventive concept 27, wherein the inner surface is configured to define a proximal converging portion that is proximal to the diverging portion of the conduit, the proximal converging portion converging in a direction from a proximal end of the converging portion to a distal end of the converging portion.

Inventive concept 31. The apparatus according to inventive concept 27, wherein the device comprises a set of one or more balloons.

Inventive concept 32. The apparatus according to inventive concept 27, wherein the ratio of the diameter of the conduit at the distal end of the diverging portion to the diameter of the conduit at the proximal end of the diverging portion is greater than 2:1.

Inventive concept 33. The apparatus according to inventive concept 27, wherein the ratio of the diameter of the conduit at the distal end of the diverging portion to the diameter of the conduit at the proximal end of the diverging portion is less than 4:1.

Inventive concept 34. The apparatus according to any one of inventive concepts 27-33, wherein, when in the non-constrained configuration, the device has a length of more than 20 mm.

Inventive concept 35. The apparatus according to inventive concept 34, wherein the length of the device is less than 70 mm.

Inventive concept 36. The apparatus according to any one of inventive concepts 27-33, wherein, when the device is in the non-constrained configuration, a difference between the diameter of the conduit at the distal end of the diverging portion to the diameter of the conduit at the proximal end of the diverging portion is greater than 3 mm.

Inventive concept 37. The apparatus according to inventive concept 36, wherein the difference between the diameter of the conduit at the distal end of the diverging portion to the diameter of the conduit at the proximal end of the diverging portion is greater than 5 mm.

Inventive concept 38. The apparatus according to inventive concept 36, wherein the difference between the diameter of the conduit at the distal end of the diverging portion to the diameter of the conduit at the proximal end of the diverging portion is less than 30 mm.

Inventive concept 39. The apparatus according to any one of inventive concepts 27-33, wherein the device is configured such that, upon the device being implanted within a longitudinal portion of the blood vessel, blood flow through the longitudinal portion of the blood vessel, via any flow path other than through the conduit, is less than 20 percent of total blood flow through the longitudinal portion of the blood vessel.

Inventive concept 40. The apparatus according to inventive concept 39, wherein the device is configured such that, upon the device being implanted within a longitudinal portion of the blood vessel, there is no blood flow through the longitudinal portion of the blood vessel, via any flow path other than through the conduit.

Inventive concept 41. The apparatus according to any one of inventive concepts 27-33, wherein the inner surface and the outer support structure are made of stent graft material.

Inventive concept 42. The apparatus according to inventive concept 41, wherein the inner surface and the outer support structure are made of respective, separate pieces of stent graft material.

Inventive concept 43. The apparatus according to inventive concept 41, wherein the inner surface and the outer support structure are made of a single continuous piece of stent graft material.

Inventive concept 44. The apparatus according to any one of inventive concepts 27-33, the device comprising a surface that, when the device is in the non-constrained configuration, is configured to extend radially outward around a full circumference of the conduit at least to a radial location of an inner surface of the outer support structure and that is configured to impede blood flow.

Inventive concept 45. The apparatus according to inventive concept 44, wherein the surface that is configured to extend to the radial location of the inner surface of the outer support structure has a permeability per unit length of less than 0.25 micrometers.

Inventive concept 46. The apparatus according to inventive concept 44, wherein the surface that is configured to extend to the radial location of the inner surface of the outer support structure comprises a distal end of the inner surface that defines the conduit.

Inventive concept 47. The apparatus according to inventive concept 44, wherein the surface that is configured to extend to the radial location of the inner surface of the outer support structure comprises a surface that is disposed around a distal end of the conduit and that extends radially outward.

Inventive concept 48. The apparatus according to inventive concept 44, wherein the surface that is configured to extend to the radial location of the inner surface of the outer support structure comprises a surface that extends radially outward and is disposed around the conduit at a longitudinal location such that at least a portion of the surface is within a proximal-most 30 percent of a length of the conduit.

Inventive concept 49. The apparatus according to inventive concept 44, wherein the device comprises two surfaces that, when the device is in the non-constrained configuration, are configured to extend around the full circumference of the conduit at least to the radial location of the inner surface of the outer support structure and that are configured to impede blood flow.

Inventive concept 50. The apparatus according to inventive concept 49, wherein the two surfaces are configured to cause blood to coagulate in a region between the two surfaces.

Inventive concept 51. The apparatus according to inventive concept 49, further comprising a filling material configured to be injected into a region between the two surfaces.

Inventive concept 52. Apparatus comprising:
an implantable device configured to be deployed in a longitudinal portion of a blood vessel of a subject, the device comprising:
an inner surface that is configured, when the device is in a deployed state within the longitudinal portion of the blood vessel, to define a conduit through the device from a proximal end of the device to a distal end of the device, at least a portion of the inner surface diverging in a direction from a proximal end of the diverging portion to a distal end of the diverging portion, such that a cross-sectional area of the diverging portion at its distal end is greater than the cross-sectional area of the diverging portion at its proximal end,
the device being configured, upon being deployed inside the longitudinal portion of the blood vessel, to direct blood flow through the longitudinal portion of the blood vessel via the conduit, such that blood flow through the longitudinal portion of the blood vessel, via any flow path other than through the conduit, is less than 20 percent of total blood flow through the longitudinal portion of the blood vessel.

Inventive concept 53. The apparatus according to inventive concept 52, wherein the device does not include a prosthetic valve.

Inventive concept 54. The apparatus according to inventive concept 52, wherein the device is configured such that, upon the device being implanted within the longitudinal portion of the blood vessel, there is no blood flow through the longitudinal portion of the blood vessel, via any flow path other than through the conduit.

Inventive concept 55. The apparatus according to inventive concept 52, wherein the device is configured such that, upon the device being implanted within a longitudinal portion of an ascending aorta of the subject, the device reduces pressure loss within the ascending aorta relative to pressure loss within the ascending aorta in an absence of the device.

Inventive concept 56. The apparatus according to inventive concept 52, wherein the inner surface is configured to define a proximal converging portion that is proximal to the diverging portion of the conduit, the proximal converging portion converging in a direction from a proximal end of the converging portion to a distal end of the converging portion.

Inventive concept 57. The apparatus according to inventive concept 52, wherein the device comprises a set of one or more balloons.

Inventive concept 58. The apparatus according to any one of inventive concepts 52-57, wherein the device is configured such that, when in the deployed state within the longitudinal portion of the blood vessel, the device has a length of more than 20 mm.

Inventive concept 59. The apparatus according to inventive concept 58, wherein the device is configured such that the length of the device is less than 70 mm.

Inventive concept 60. The apparatus according to any one of inventive concepts 52-57, wherein the device is configured such that, when the device is in the deployed state within the longitudinal portion of the blood vessel, a difference between a diameter of the conduit at the proximal end of the diverging portion to a diameter of the conduit at the distal end of the diverging portion is greater than 3 mm.

Inventive concept 61. The apparatus according to inventive concept 60, wherein the device is configured such that the difference between the diameter of the conduit at the distal end of the diverging portion to the diameter of the conduit at the proximal end of the diverging portion is greater than 5 mm.

Inventive concept 62. The apparatus according to inventive concept 60, wherein the device is configured such that the difference between the diameter of the conduit at the distal end of the diverging portion to the diameter of the conduit at the distal end of the diverging portion is less than 30 mm.

Inventive concept 63. The apparatus according to any one of inventive concepts 52-57, wherein the device is configured such that, when the device is in the deployed state within the longitudinal portion of the blood vessel, a ratio of a diameter of the conduit at a distal end of the diverging portion to a diameter of the conduit at a proximal end of the diverging portion is greater than 4:3.

Inventive concept 64. The apparatus according to inventive concept 63, wherein the device is configured such that the ratio of the diameter of the conduit at the distal end of the diverging portion to the diameter of the conduit at the proximal end of the diverging portion is greater than 2:1.

Inventive concept 65. The apparatus according to inventive concept 63, wherein the device is configured such that the ratio of the diameter of the conduit at the distal end of the diverging portion to the diameter of the conduit at the proximal end of the diverging portion is less than 4:1.

Inventive concept 66. The apparatus according to any one of inventive concepts 52-57, wherein the device comprises an outer support structure configured to maintain the device inside the blood vessel by contacting the inner wall of the blood vessel.

Inventive concept 67. The apparatus according to inventive concept 66, wherein the device is configured such that, when the device is in the deployed state within the longitudinal portion of the blood vessel, a ratio between an outer diameter of a proximal end of the outer support structure and an outer diameter of a distal end of the outer support structure is between 3:4 and 4:3.

Inventive concept 68. The apparatus according to inventive concept 66, wherein the inner surface and the outer support structure are made of stent graft material.

Inventive concept 69. The apparatus according to inventive concept 68, wherein the inner surface and the outer support structure are made of respective, separate pieces of stent graft material.

Inventive concept 70. The apparatus according to inventive concept 68, wherein the inner surface and the outer support structure are made of a single continuous piece of stent graft material.

Inventive concept 71. The apparatus according to inventive concept 66, the device comprising a surface that, when the device is in the deployed state within the longitudinal portion of the blood vessel, is configured to extend radially outward around a full circumference of the conduit at least to a radial location of an inner surface of the outer support structure, and that is configured to impede blood flow.

Inventive concept 72. The apparatus according to inventive concept 71, wherein the surface that is configured to extend to the radial location of the inner surface of the outer support structure has a permeability per unit length of less than 0.25 micrometers.

Inventive concept 73. The apparatus according to inventive concept 71, wherein the surface that is configured to extend to the radial location of the inner surface of the outer support structure comprises a distal end of the inner surface that defines the conduit.

Inventive concept 74. The apparatus according to inventive concept 71, wherein the surface that is configured to extend to the radial location of the inner surface of the outer support structure comprises a surface that is disposed around a distal end of the conduit and that is configured to extend radially outward.

Inventive concept 75. The apparatus according to inventive concept 71, wherein the surface that is configured to extend to the radial location of the inner surface of the outer support structure comprises a surface that is configured to extend radially outward and that is disposed around the conduit at a longitudinal location such that at least a portion of the surface is within a proximal-most 30 percent of a length of the conduit.

Inventive concept 76. The apparatus according to inventive concept 71, wherein the device comprises two surfaces that are configured to extend radially outward around the full circumference of the conduit at least to the radial location of the inner surface of the outer support structure and that are configured to impede blood flow.

Inventive concept 77. The apparatus according to inventive concept 76, wherein the two surfaces are configured to cause blood to coagulate in a region between the two surfaces.

Inventive concept 78. The apparatus according to inventive concept 76, further comprising a filling material configured to be injected into a region between the two surfaces.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
   an implantable device comprising a graft material that comprises a stent and fabric, the device being configured to be deployed in an ascending aorta of a subject, and the device comprising:
   a proximal end configured to be disposed in the ascending aorta spaced apart from an aortic valve of the subject;
   a distal end; an inner surface,
   wherein the stent is shape set such that, throughout deployment of the device within a longitudinal portion of the ascending aorta, the inner surface defines a conduit extending through the device from the proximal end of the device to the distal end of the device, the conduit including a diverging portion that diverges in a direction from a proximal end of the conduit to a distal end of the conduit, such that a cross-sectional area of the conduit at a distal end of the diverging portion is greater than the cross-sectional area of the conduit at a proximal end of the diverging portion,
   the conduit being configured to reduce pressure loss of blood flowing through the conduit, relative to a loss of pressure of blood flowing through the longitudinal portion of the ascending aorta in the absence of the device, in a passive manner, by reducing an area of flow separation of the blood flow; and
   an outer support structure configured, when the device is in a deployed state within the longitudinal portion of the ascending aorta, to at least partially overlap with the inner surface that defines the conduit, and to maintain the device within the ascending aorta by contacting an inner wall of the ascending aorta,
   the device, when in the deployed state within the longitudinal portion of the ascending aorta, being configured to define, at its distal end, a region including an outer circumference that apposes the inner wall of the ascending aorta, the region being configured to impede backflow of blood, outside of the conduit, toward the aortic valve.

2. The apparatus according to claim 1, wherein, the implantable device is configured such that, during systole of the subject's cardiac cycle, blood is configured to flow in an antegrade direction through the diverging portion of the conduit into the ascending aorta.

3. The apparatus according to claim 1, wherein, the implantable device is configured such that, during diastole of the subject's cardiac cycle, blood is configured to flow in a retrograde direction through the diverging portion of the conduit toward coronary arteries of the subject.

4. The apparatus according to claim 1, wherein the device does not include a prosthetic valve.

5. The apparatus according to claim 1, wherein the device comprises a surface extending radially outward around a full circumference of the conduit, from the conduit at least to a radial location of an inner surface of the outer support structure, the surface that extends radially outward having a permeability per meter of less than 0.25 micrometers.

6. The apparatus according to claim 1, wherein a distal end of the inner surface that defines the conduit is configured to appose the inner wall of the ascending aorta.

7. The apparatus according to claim 1, wherein a surface that is disposed around a distal end of the conduit and that extends radially outward is configured to appose the inner wall of the ascending aorta.

8. The apparatus according to claim 1, wherein the device is configured such that, when the device is in the deployed state within the longitudinal portion of the ascending aorta, a ratio between an outer diameter of a proximal end of the outer support structure and an outer diameter of a distal end of the outer support structure is between 3:4 and 4:3.

9. The apparatus according to claim 1, wherein the inner surface is configured to define a proximal converging portion that is proximal to the diverging portion of the conduit, the proximal converging portion converging in a direction from a proximal end of the converging portion to a distal end of the converging portion.

10. The apparatus according to claim 1, wherein the device is configured such that, upon the device being implanted within a longitudinal portion of the ascending aorta, blood flow through the longitudinal portion of the ascending aorta, via any flow path other than through the conduit, is less than 20 percent of total blood flow through the longitudinal portion of the ascending aorta.

11. The apparatus according to claim 10, wherein the device is configured such that, upon the device being implanted within a longitudinal portion of the ascending aorta, there is no blood flow through the longitudinal portion of the ascending aorta, via any flow path other than through the conduit.

12. The apparatus according to claim 1, wherein the inner surface and the outer support structure are made of stent graft material.

13. The apparatus according to claim 12, wherein the inner surface and the outer support structure are made of respective, separate pieces of stent graft material.

14. The apparatus according to claim 12, wherein the inner surface and the outer support structure are made of a single continuous piece of stent graft material.

15. The apparatus according to claim 1, wherein the device is configured such that, when the device is in the deployed state within the longitudinal portion of the ascending aorta, the device defines two surfaces that extend radially outward, around the full circumference of the conduit, and that are configured to appose the inner wall of the ascending aorta.

16. The apparatus according to claim 15, wherein the two surfaces are configured to cause blood to coagulate in a region between the two surfaces.

17. The apparatus according to claim 15, further comprising a filling material configured to be injected into a region between the two surfaces.

18. The apparatus according to claim 1, wherein the device is configured such that, when the device is in the deployed state within the longitudinal portion of the blood vessel, a ratio of a diameter of the conduit at a distal end of the diverging portion to a diameter of the conduit at a proximal end of the diverging portion is greater than 4:3.

19. The apparatus according to claim 18, wherein the device is configured such that the ratio of the diameter of the conduit at the distal end of the diverging portion to the diameter of the conduit at the proximal end of the diverging portion is greater than 2:1.

20. The apparatus according to claim 18, wherein the device is configured such that the ratio of the diameter of the conduit at the distal end of the diverging portion to the diameter of the conduit at the proximal end of the diverging portion is less than 4:1.

* * * * *